US008129424B2

(12) United States Patent
Bennani et al.

(10) Patent No.: US 8,129,424 B2
(45) Date of Patent: *Mar. 6, 2012

(54) INDOLE DERIVATIVES AS HISTAMINE 3 RECEPTOR INHIBITORS FOR THE TREATMENT OF COGNITIVE AND SLEEP DISORDERS, OBESITY AND OTHER CNS DISORDERS

(75) Inventors: Youssef L. Bennani, Boston, MA (US); Michael G. Campbell, Thunder Bay (CA); David Dastrup, Orem, UT (US); Emilie Porter Huck, Sudbury, MA (US)

(73) Assignee: Athersys, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/943,659

(22) Filed: Nov. 10, 2010

(65) Prior Publication Data

US 2011/0059966 A1    Mar. 10, 2011

Related U.S. Application Data

(63) Continuation of application No. 12/284,574, filed on Sep. 23, 2008, now Pat. No. 7,855,224, which is a continuation of application No. 11/581,631, filed on Oct. 16, 2006, now Pat. No. 7,528,262.

(60) Provisional application No. 60/726,793, filed on Oct. 14, 2005.

(51) Int. Cl.
*A61K 31/404* (2006.01)
*C07D 209/12* (2006.01)

(52) U.S. Cl. .................. 514/415; 548/465; 548/509
(58) Field of Classification Search .............. 548/465, 548/509
See application file for complete search history.

(56) References Cited

U.S. PATENT DOCUMENTS

| 3,799,943 | A | 3/1974 | Bell et al. |
| 5,399,599 | A | 3/1995 | Guillot |
| 5,631,381 | A | 5/1997 | Huang et al. |
| 6,630,496 | B1 | 10/2003 | Seehra et al. |
| 2007/0287715 | A1* | 12/2007 | Olofsson et al. ......... 514/254.09 |

FOREIGN PATENT DOCUMENTS

| WO | 93/25524 | 12/1993 |
| WO | 99/43672 | 9/1999 |
| WO | 2004/099192 | 11/2004 |

OTHER PUBLICATIONS

Stroke [online] retrieved from the internet on Jun. 20, 2011. URL; http://www.ncbi.nlm.nih.gov/pubmedhealth/PMH0001740/.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/Health/conditions/O9/24/alzheimers.drug.ap/indexhtml>.*
Arrang et al., "Auto-inhibition of brain histamine release mediated by a novel class (H3) of histamine receptor", Nature vol. 302 Apr. 28, 1983, pp. 832-837.
Berge et al., "Pharmaceutical Salts", Journal of Pharmaceutical Sciences Jan. 1977 vol. 66 No. 1, pp. 1-19.
Carreno et al., "Enantioselective diels-alder cycloadditions with (SS)-2-(p-Tolylsulfinyl)-1,4-naphthoquinone: efficient kinetic resolution of chiral racemic vinylcyclohexenes", J. Org. Chem. 1998, 63, pp. 8320-8330.
Coward et al., "Chimeric G proteins allow a high-throughput signaling assay of Gi-coupled receptors", Analytical Biochemistry 270, 1999, pp. 242-248.
Cowart et al., "Medicinal Chemistry and Biological Properties of Non-Imidazole Histamine H3 Antagonists", Mini-Reviews in Medicinal Chemistry, 2004, 4, 979-992, Bentham Science Publishers Ltd.
Esbenshade et a. "Histamine H3 Receptor Antagonists: Preclinical Promis for Treating Obesity and Cognitive Disorders", Molecular Interventions, vol. 6, Issue 2, Apr. 2006, Abbott Laboratories, Division of Neuroscience Research, Global Pharmaceutical Research and Development.
Harrington et al., "Creation of genome-wide protein expression libraries using random activation of gene expression", Nature Publishing Group, May 2001, vol. 19, pp. 440-445.
Inagaki et al., "Organization of histaminergic fibers in the rat brain", The Journal of Comparative Neurology, 1988 No. 273 pp. 283-300.
Klapars et al., "A general and efficient copper catalyst for the amidation of aryl halides and the N-arylation of nitrogen heterocycles", J. Am. Chem. Soc. 2001 No. 123, pp. 7727-7729.
Kuyper et al., "High-affinity inhibitors of dihydrofolate reductase: antimicrobial and anticancer activities of 7,8-dialky1-1,3-diaminopyrrolo[3,2-f]quinazolines with small molecular size", J. Med. Chem. 1996, No. 39, pp. 892-903.
Leurs et al., "The Histamine H3 Receptor: From Gene Cloning to H3 Receptor Drugs", Nature Reviews, vol. 4, Feb. 2005, Divisional of Medicinal Chemistry, Leiden/Amsterdam Center for Drug Research.
Lin et al., "Involvement of histaminergic neurons in arousal mechanisms demonstrated with H3-receptor ligands in the cat", Brain Research, 1990 No. 523, pp. 325-330.
Poste et al., "Lipid vesicles as carriers for introducing biologically active materials into cells", National Library of Medicine, Dec. 28, 1976, pp. 1-22.
Schwartz, "Minireview histamine as a transmitter in brain", Life Science vol. 17, pp. 503-518.
Schwartz et al., "Three classes of histamine receptors in brain", TIPS 1986, pp. 24-28.

* cited by examiner

*Primary Examiner* — Shawquia Young
(74) *Attorney, Agent, or Firm* — Wood, Phillips, Katz, Clark & Mortimer

(57) ABSTRACT

This invention relates to compounds having pharmacological activity, to compositions containing these compounds, and to a method of treatment employing the compounds and compositions. More particularly, this invention concerns certain indole derivatives and their salts and solvates. These compounds have $H_3$ histamine receptor antagonist activity. This invention also relates to pharmaceutical compositions containing these compounds and to a method of treating disorders in which histamine $H_3$ receptor blockade is beneficial.

3 Claims, No Drawings

INDOLE DERIVATIVES AS HISTAMINE 3 RECEPTOR INHIBITORS FOR THE TREATMENT OF COGNITIVE AND SLEEP DISORDERS, OBESITY AND OTHER CNS DISORDERS

CROSS REFERENCE TO RELATED APPLICATION

This application is a continuation application of the U.S. nonprovisional application Ser. No. 12/284,574 filed Sep. 23, 2008 which is a continuation of U.S. nonprovisional application Ser. No. 11/581,631 filed Oct. 16, 2006 which claims priority of U.S. provisional patent application Ser. No. 60/726,793 filed Oct. 14, 2005, the disclosure of which is incorporated herein by reference.

TECHNICAL FIELD

This invention relates to compounds having pharmacological activity, to compositions containing these compounds, and to a method of treatment employing the compounds and compositions. More particularly, this invention concerns certain indole derivatives and their salts and solvates. These compounds alter $H_3$ histamine receptor activity. This invention also relates to pharmaceutical compositions containing these compounds and to a method of treating disorders in which histamine $H_3$ receptor blockade is beneficial.

BACKGROUND OF THE INVENTION

Histamine is a chemical messenger involved in various complex biological actions. When released, histamine interacts with specific macromolecular receptors on the cell surface or within a target cell to elicit changes in many different bodily functions. Various cell types including smooth muscle, blood cells, cells of the immune system, endocrine and exocrine cells as well as neurons respond to histamine by modulating the formation of intracellular signals, including of phosphatidylinositol, or adenylate cyclase. Evidence that histamine plays a role as a neurotransmitter was established by the mid-to-late 1970's (Schwartz, 1975) *Life Sci.* 17:503-518. Immunohistochemical studies identified histaminergic cell bodies in the tuberomammillary nucleus of the posterior hypothalamus with widespread projections in the dicencephalon and telencephalon (Inagaki et al., 1998) *J. Comp. Neural.* 273:283-300.

Two histamine receptors ($H_1$ and $H_2$) were reported to mediate the biochemical actions of histamine on neurons. More recently, studies have demonstrated the existence of a third subtype of histamine receptor, the histamine $H_3$ receptor (Schwartz et al., 1986) *TIPS* 8: 24-28. Various studies have now demonstrated that histamine $H_3$ receptors are found on the histaminergic nerve terminals in the brains of several species, including man (Arrang et al., 1983) *Nature* 302: 832-837. The $H_3$ receptor found on the histaminergic nerve terminal was defined as an autoreceptor and could intimately control the amount of histamine released from the neurons. Histamine, the natural compound, was capable of stimulating this autoreceptor but testing of known $H_1$ and $H_2$ receptor agonists and antagonists suggested that the $H_3$ receptor has a distinct pharmacological profile. Further, $H_3$ receptors have been identified on cholinergic, serotoninergic and monoamine nerve terminals in the peripheral nervous system (PNS) and central nervous system including the cerebral cortex and cerebral vessels. These observations suggest that $H_3$ receptors are uniquely located to modulate histamine as well as other neurotransmitter release, and compounds that bind $H_3$ receptors could be important mediators of neuronal activity.

As stated, CNS histaminergic cell bodies are found in the magnocellular nuclei of the hypothalamic mammillary region and these neurons project diffusely to large areas of the forebrain. The presence of histaminergic cell bodies in the tuberomammillary nucleus of the posterior hypothalamus, a brain area involved in the maintenance of wakefulness, and their projections to the cerebral cortex suggest a role in modulating the arousal state or sleep-wake cycle. The histaminergic projection to many limbic structures such as the hippocampal formation and the amygdaloid complex suggest roles in functions such as autonomic regulation, control of emotions and motivated behaviors, and memory processes.

The concept that histamine is important for the state of arousal, as suggested by the location of histaminergic pathways, is supported by other types of evidence. Lesions of the posterior hypothalamus are well known to produce sleep. Neurochemical and electrophysiological studies have also indicated that the activity of histaminergic neurons is maximal during periods of wakefulness and is suppressed by barbiturates and other hypnotics. Intraventricular histamine induces the appearances of an arousal EEG pattern in rabbits and increased spontaneous locomotor activity, grooming and exploratory behavior in both saline and pentobarbital-treated rats.

In contrast, a highly selective inhibitor of histidine decarboxylase, the sole enzyme responsible for histamine synthesis, has been shown to impair waking in rats. These data support the hypothesis that histamine may function in modulating behavioral arousal. The role of the $H_3$ receptor in sleep-waking parameters has been demonstrated (Lin et al., 1990) *Brain Res.* 592: 325-330. Oral administration of RAMHA, a $H_3$ agonist, caused a significant increase in deep slow wave sleep in the cat. Conversely, thioperamide, a $H_3$ antagonist/inverse agonist, enhanced wakefulness in a dose-dependent fashion. Thioperamide has also been shown to increase wakefulness and decrease slow-wave and REM sleep in rats. These findings are consistent with in vivo studies demonstrating that thioperamide caused an increase in synthesis and release of histamine. Together, these data demonstrate that selective $H_3$ antagonists or inverse agonists may be useful in the treatment of arousal states and sleep disorders.

Serotonin, histamine, and acetylcholine have all been demonstrated to be diminished in the Alzheimer's (AD) brain. The histamine $H_3$ receptor has been demonstrated to regulate the release of each of these neurotransmitters. An $H_3$ receptor antagonist or inverse agonist would therefore be expected to increase the release of these neurotransmitters in the brain. Since histamine has been demonstrated to be important in arousal and vigilance, $H_3$ receptor antagonists or inverse agonists might enhance arousal and vigilance via increasing levels of neurotransmitter release and thereby improve cognition. Thus, the use of compounds that bind the use of $H_3$ receptor in AD, attention deficit disorders (ADD), age-related memory dysfunction and other cognitive disorders would be supported.

$H_3$ receptor antagonists or inverse agonists may be useful in treating several other CNS disorders. It has been suggested that histamine may be involved in cerebral circulation, energy metabolism, and hypothalmic hormone secretion. For example, $H_3$ receptor antagonists or inverse agonists have been demonstrated to affect food intake and body weight gain in rodents. Recent evidence has indicated the possible use of $H_3$ antagonists or inverse agonists in the treatment of epilepsy. Work has demonstrated an inverse correlation between the duration of clonic convulsions and brain histamine levels.

Thioperamide was also shown to significantly and dose-dependently decrease the durations of every convulsive phase after electrically-induced convulsions and increase the electroconvulsive threshold.

In spite of their low density, $H_3$ receptor binding sites can be detected outside the brain. Several studies have revealed the presence of $H_3$ heteroreceptors in the gastrointestinal tract, as well as upon neurons of the respitory tract. Accordingly, an $H_3$ receptor binding compound may be useful in the treatment of diseases and conditions such as asthma, rhinitis, airway congestion, inflammation, hyper and hypo motility and acid secretion of the gastrointestinal tract. Peripheral or central blockage of $H_3$ receptors may also contribute to changes in blood pressure, heart rate and cardiovascular output and could be used in the treatment of cardiovascular diseases, and in the treatment of diseases or conditions such as obesity, migraine, inflammation, motion sickness, pain, ADHD, dementia, depression, Parkinson's disease, schizophrenia, epilepsy, narcolepsy, acute myocardial infarction and asthma.

Various indole derivatives are disclosed in U.S. Pat. Nos. 5,631,381 and 6,630,496 B1; WO 93/25524; WO 99/43672 and WO 2004/099192.

SUMMARY OF THE INVENTION

The present invention provides, in its principal aspect, compounds of the general formula:

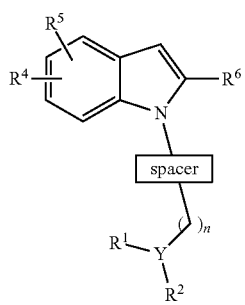

wherein spacer is

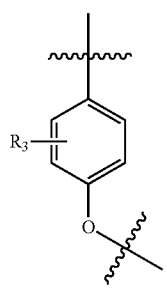

A

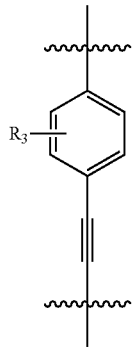

B

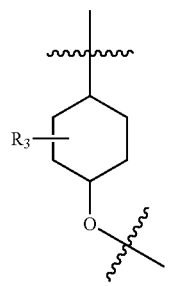

C

Y is CH or N, provided that if Y is CH then n is 0-2; if Y is N then n is 2-4;

if Y is CH then $R^1$ and $R^2$ taken together are —$(CH_2)_a$—$NR^{11}$—$(CH_2)_2$— where a is 1-2 which when taken together with Y form a piperidine or pyrrolidine ring which is optionally substituted with 1-3 groups selected from fluoro, fluoroalkyl, $(C_1-C_4)$alkyl, alkoxy, aryl, $(C_3-C_7)$cycloalkyl, heterocycloalkyl containing 1-2 hetero atoms selected from (O, S) and $(C_1-C_5)$alkyl-O—$(C_1-C_5)$alkyl; and if Y is N then $R^1$ and $R^2$ independently are $(C_1-C_5)$alkyl or $(C_3-C_6)$cycloalkyl, or R' and $R^2$ taken together with the nitrogen to which they are attached form a 5-7 member heterocyclic ring system with 0-1 additional hetero atoms selected from O and S which is optionally substituted with 1-3 $(C_1-C_5)$alkyl, fluoroalkyl or $(C_3-C_6)$cycloalkyl groups, or $R^1$ and $R^2$ taken together are —$(CH_2)_a$—$NR^{11}$—$(CH_2)_2$—, where a is 2-3, which when taken together with Y form a piperazine or homopiperazine ring which is optionally substituted with 1-3 groups selected from fluoro, fluoroalkyl, $(C_1-C_4)$alkyl, alkoxy, aryl, $(C_3-C_7)$cycloalkyl, heterocycloalkyl containing 1-2 hetero atoms selected from (O, S) and $(C_1-C_5)$alkyl-O—$(C_1-C_5)$alkyl;

$R^3$ is 0-2 of groups selected from halogen, $(C_1-C_6)$alkyl, $(C_1-C_6)$alkoxy, $(C_3-C_7)$cycloalkyl, $(C_3-C_7)$cycloalkyl-$(C_1-C_6)$alkyl, heterocycloalkyl containing 1-3 hetero atoms selected from (O, S) and $(C_1-C_3)$alkyl-O—$(C_1-C_5)$alkyl;

$R^4$ and $R^5$ are selected independently from H, $(C_1-C_5)$alkyl, $(C_1-C_8)$alkoxy, $(C_1-C_5)$alkyl-O—$(C_1-C_5)$alkyl, $(C_3-C_6)$cycloalkyl, aryl, $CF_3$ and halogen;

$R^6$ is $CONR^7R^8$, —$(CH_2)_x$—O—$R^9$, alkyl, fluoroalkyl or $SO_2NR^7R^8$;

x is 1-4;

$R^7$ and $R^8$ independently are hydrogen, $(C_1-C_5)$alkyl or $(C_3-C_6)$cycloalkyl, or $R^7$ and $R^8$ together with the nitrogen to which they are attached form a 5-7 member heterocyclic ring system with 0-1 additional hetero atoms selected from O, S and $N(R^{10}$, wherein the resulting ring is optionally substituted with 1-3 $(C_1-C_5)$alkyl or $(C_3-C_6)$cycloalkyl groups;

$R^9$ is hydrogen, $(C_1-C_5)$alkyl, $(C_3-C_7)$cycloalkyl or aryl;

$R^{10}$ is $(C_1-C_5)$alkyl, $(C_1-C_8)$alkoxy, $(C_1-C_5)$alkyl-O—$(C_1-C_5)$alkyl, $(C_3-C_6)$cycloalkyl or aryl; and $R^{11}$ is $(C_1-C_5)$alkyl, fluoroalkyl or $(C_3-C_6)$cycloalkyl and the pharmaceutically acceptable salts, and individual stereoisomers thereof.

This invention also provides pharmaceutical compositions comprising a pharmaceutically acceptable carrier in combination with an effective amount of at least one compound of formula (I).

The present invention also provides a method of treating conditions in which modulation of histamine $H_3$ receptors may be of therapeutic importance such as inflammation, migraine, motion sickness, pain, Parkinson's Disease, epilepsy, cardiovascular disease (i.e. hyper or hypotension, acute myocardial infarction), gastrointestinal disorders (acid secretion, motility) and CNS disorders involving attention or cognitive disorders (i.e., Alzheimer's, Attention Deficit Disorder, age-related memory dysfunction, stroke, etc.), psychiatric disorders (i.e., depression, schizophrenia, obsessive-compulsive disorders, etc.); sleep disorders (i.e. narcolepsy, sleep apnea, insomnia, disturbed biological and circadian rhythms, hyper- and hyposomnolence), and disorders such as obesity, anorexia/bulimia, thermoregulation, hormone release) comprising administering an effective amount of a compound of formula (I) to a patient in need of such treatment.

DETAILED DESCRIPTION OF THE INVENTION

Preferably for compounds of formula (I), $R^1$—Y—$R^2$ is

$R^3$ is H; $R^4$ is H; 5-methoxy, 5-fluoro or methyl; $R^5$ is H; and $R^6$ is —$CH_2OCH_3$ or —$(CH_2)_2OCH_3$.

Presently preferred compounds include:
2-Methyl-1-[4-(3-pyrrolidin-1-ylpropoxy)phenyl]-1H-indole;
-Methyl-1-[4-(3-piperidin-1-ylpropoxy)phenyl]-1H-indole;
2-Methyl-1-{4-[3-(2R-methylpyrrolidin-1-yl)propoxy]phenyl}-1H-indole;
1-[4-(3-Pyrrolidin-1-ylpropoxy)phenyl]-1H-indole;
5-Methoxy-2-methyl-1-[4-(3-pyrrolidin-1-ylpropoxy)phenyl]-1H-indole;
5-Methyl-1-[4-(3-pyrrolidin-1-ylpropoxy)phenyl]-1H-indole;
5-Bromo-1-[4-(3-pyrrolidin-1-ylpropoxy)phenyl]-1H-indole;
4-Chloro-1-[4-(3-pyrrolidin-1-ylpropoxy)phenyl]-1H-indole;
5-Methoxy-1-[4-(3-pyrrolidin-1-ylpropoxy)phenyl]-1H-indole;
5-Chloro-1-[4-(3-pyrrolidin-1-ylpropoxy)phenyl]-1H-indole;
2,5-Dimethyl-1-[4-(3-pyrrolidin-1-ylpropoxy)phenyl]-1H-indole;
6-Chloro-1-[4-(3-pyrrolidin-1-ylpropoxy)phenyl]-1H-indole;
2-Methyl-5-fluoro-1-[4-(3-pyrrolidin-1-ylpropoxy)phenyl]-1H-indole;
1-[3-Methoxy-4-(3-pyrrolidin-1-ylpropoxy)phenyl]-2-methyl-1H-indole;
1-[3-Chloro-4-(3-pyrrolidin-1-ylpropoxy)phenyl]-2-methyl-1H-indole;
2-Propyl-1-[4-(3-pyrrolidin-1-ylpropoxy)phenyl]-1H-indole;
5-Methoxy-2-methyl-1-[4-(4-pyrrolidin-1-ylbut-1-ynyl)phenyl]-1H-indole;
(5-Methoxy-1-{4-[3-(2R-methylpyrrolidin-1-yl)propoxy]phenyl}-1H-indol-2-yl)pyrrolidin-1-ylmethanone;
1-{4-[3-(2R-Methylpyrrolidin-1-yl)propoxy]phenyl}-1H-indole-2-carboxylic acid cyclobutylamide;
1-{4-[3-(2R-Methylpyrrolidin-1-yl)propoxy]phenyl}-1H-indole-2-carboxylic acid cyclopentylamide;
1-{4-[3-(2R-Methylpyrrolidin-1-yl)propoxy]phenyl}-1H-indole-2-carboxylic acid cyclohexylamide;
1-{4-[3-(2R-Methylpyrrolidin-1-yl)propoxy]phenyl}-1H-indole-2-carboxylic acid cycloheptylamide;
1-{4-[3-(2R-Methylpyrrolidin-1-yl)propoxy]phenyl}-1H-indol-2-yl)pyrrolidin-1-ylmethanone;
2-(3-Morpholin-4-ylpropoxy)-6,7,8,9-tetrahydropyrido[1,2-a]indole;
(1-{4-[3-(2R-Methylpyrrolidin-1-yl)propoxy]phenyl}-1H-indol-2-yl)morpholin-4-ylmethanone;
1-{4-[3-(2R-Methylpyrrolidin-1-yl)propoxy]phenyl}-1H-indole-2-carboxylic acid butylamide;
1-{4-[3-(2R-Methylpyrrolidin-1-yl)propoxy]phenyl}-1H-indole-2-carboxylic acid isobutylamide;
1-{4-[3-(2R-Methylpyrrolidin-1-yl)propoxy]phenyl}-1H-indole-2-carboxylic acid cyclohexylmethylamide;
5-Methoxy-1-{4-[3-(2R-methylpyrrolidin-1-yl)propoxy]phenyl}-1H-indole-2-carboxylic acid cyclohexylamide;
1-[4-(3-Pyrrolidin-1-ylpropoxy)phenyl]-1H-indole-2-carboxylic acid ethyl ester;
{1-[4-(3-Pyrrolidin-1-ylpropoxy)phenyl]-1H-indol-2-yl}methanol;
2-Methoxymethyl-1-[4-(3-pyrrolidin-1-ylpropoxy)phenyl]-1H-indole;
2-Cyclohexyloxymethyl-1-[4-(3-pyrrolidin-1-ylpropoxy)phenyl]-1H-indole;
2-Isopropoxymethyl-1-[4-(3-pyrrolidin-1-ylpropoxy)phenyl]-1H-indole;
2-Cyclopentyloxymethyl-1-[4-(3-pyrrolidin-1-ylpropoxy)phenyl]-1H-indole;
{5-Methoxy-1-[4-(3-pyrrolidin-1-ylpropoxy)phenyl]-1H-indol-2-yl}methanol;
2-Cyclopropyl-1-[4-(3-pyrrolidin-1-ylpropoxy)phenyl]-1H-indole;
2-Propyl-1-[4-(3-pyrrolidin-1-ylpropoxy)phenyl]-1H-indole;
2-Cyclopropyl-1-[4-(3-pyrrolidin-1-ylpropoxy)cyclohexyl]-1H-indole;
2-(2-Methoxyethyl)-1-[4-(3-pyrrolidin-1-ylpropoxy)phenyl]-1H-indole; and
2-{1-[4-(3-Pyrrolidin-1-ylpropoxy)phenyl]-1H-indol-2-yl}ethanol.

Certain compounds of the invention may exist in different isomeric (e.g. enantiomers and distereoisomers) forms. The invention contemplates all such isomers both in pure form and in a mixture, including racemic mixtures. Enol and tautomeric forms are also included.

The compounds of the invention can exist in unsolvated as well as solvated forms, including hydrated forms, e.g., hemihydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide, potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1-19 (1977) which is incorporated herein by reference.

As throughout this specification and appended claims, the following terms have the meanings ascribed to them:

The term "alkyl" as used herein refers to straight or branched chain radicals derived from saturated hydrocarbons by the removal of one hydrogen atom. Representative examples of alkyl groups include methyl, ethyl, n-propyl, iso-propyl, n-butyl, sec-butyl, iso-butyl, tert-butyl, and the like.

The term "cycloalkyl" as used herein refers to an aliphatic ring system having 3 to 10 carbon atoms and 1 to 3 rings, including, but not limited to cyclopropyl, cyclopentyl, cyclohexyl, norbornyl, and adamantly among others. Cycloalkyl groups can be unsubstituted or substituted with one, two or three substituents independently selected from lower alkyl, haloalkyl, alkoxy, thioalkoxy, amino, alkylamino, dialkylamino, hydroxyl, halo, mercapto, nitro, carboxaldehyde, carboxy, alkoxycarbonyl and carboximide.

"Cycloalkyl" includes cis or trans forms. Furthermore, the substituents may either be in endo or exo positions in the bridged bicyclic systems.

The term "halo" or "halogen" as used herein refers to I, Br, Cl or F.

The term "heteroatom" as used herein refers to at least one N, O or S atom.

The term "heterocyclyl" as used herein, alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

As used herein, the term "composition" is intended to encompass a product comprising the specified ingredients in the specified amounts, as well as any product which results, directly or indirectly, from a combination of the specified ingredients in the specified amounts.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; (f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

Compounds of the present invention that are formed by in vivo conversion of a different compound that was administered to a mammal are intended to be included within the scope of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The invention may be illustrated by the following representative scheme and examples.

Scheme 1

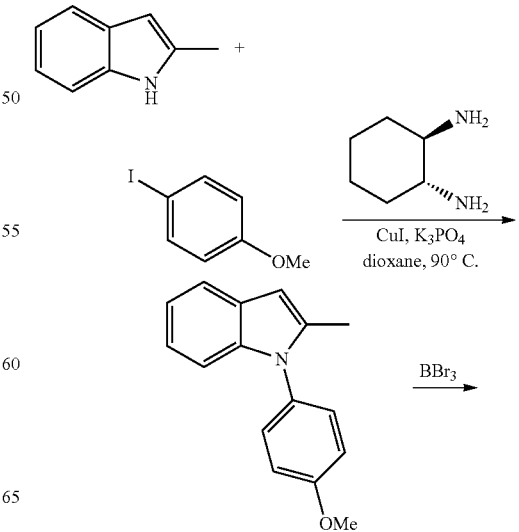

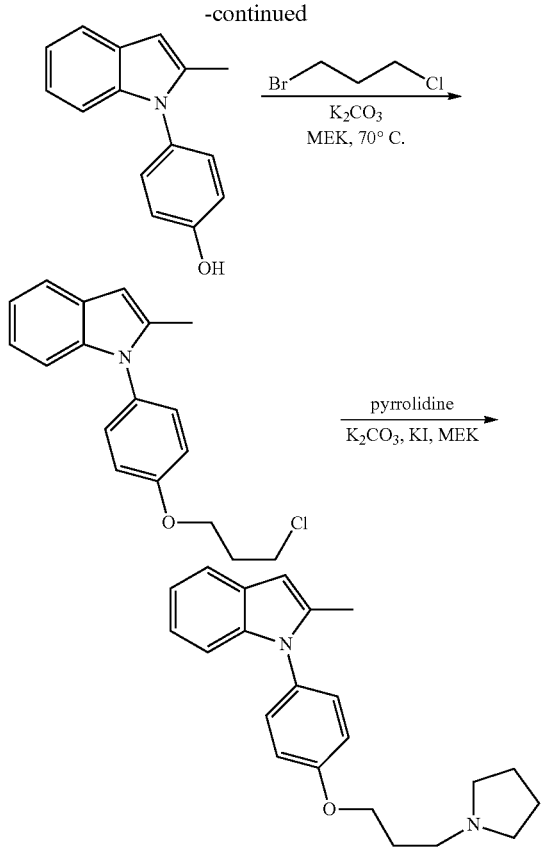

Example 1

2-Methyl-1-[4-(3-pyrrolidin-1-ylpropoxy)phenyl]-1H-indole

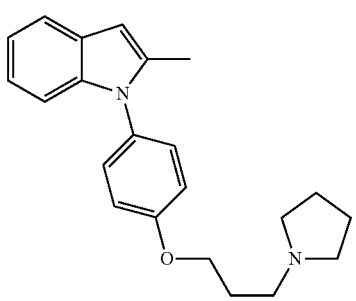

1-(4-Methoxyphenyl)-2-methyl-1H-indole. 1-(4-Methoxyphenyl)-2-methyl-1H-indole was synthesized according to Buchwald et al. *J. Am. Chem. Soc.* 2001, 123, 7727. 2-Methylindole (157 mg, 1.2 mmol), 4-iodoanisole (234 mg, 1 mmol), copper(I) iodide (2 mg, 0.01 mmol), trans-1,2-diaminocyclohexane (11.4 mg, 0.1 mmol), and potassium phosphate tribasic (446 mg, 2.1 mmol) were stirred in dioxane (1 mL) at 90° C. overnight. The reaction mixture was filtered through a pad of silica and washed with ethyl acetate. SiO$_2$ chromatography with 5-20% ethyl acetate/hexanes gave 175 mg of the desired product (74% yield). LC-MS (C$_{16}$H$_{15}$NO calc'd 237) m/z 238 (M+H).

4-(2-Methylindol-1-yl)phenol. 1-(4-Methoxyphenyl)-2-meth 4-1H-indole (175 mg, 0.73 mmol) was dissolved in dichloromethane (2 mL) and cooled to 0° C. Boron tribromide (2.19 mL, 1 M solution in dichloromethane, 2.19 mmol) was added dropwise, and the reaction was stirred for 2 hours. The reaction was quenched by addition of saturated sodium bicarbonate solution, then extracted with dichloromethane followed by ethyl acetate. The organic extracts were dried over MgSO$_4$ and concentrated. The reaction was assumed to be quantitative. LC-MS (C$_{15}$H$_{13}$NO calc'd 223) m/z 224 (M+H).

1-[4-(3-Chloropropoxy)phenyl]-2-methyl-1H-indole. 4-(2-Methylindol-1-yl)phenol (0.36 mmol) was heated at 70° C. in 2-butanone (3 mL) with 1-bromo-3-chloropropane (0.107 mL, 1.08 mmol) and potassium carbonate (0.15 g, 1.08 mmol) overnight. The solvent was evaporated. The resulting residue was diluted with ethyl acetate and washed with saturated ammonium chloride solution. The aqueous layer was back-extracted with ethyl acetate. The organic extracts were dried over MgSO$_4$ and concentrated. SiO$_2$ chromatography with 5-20% ethyl acetate/hexanes gave the desired product as a colorless oil, 60 mg (56% yield, 2 steps). LC-MS (C$_{18}$H$_{18}$ClNO calc'd 299) m/z 300, 302 (M+H).

2-Methyl-1-[4-(3-pyrrolidin-1-ylpropoxy)phenyl]-1H-indole. 1-[4-(3-Chloropropoxy)phenyl]-2-methyl-1H-indole (20 mg, 0.067 mmol) was dissolved in N-methylpyrrolidinone (0.5 mL), and pyrrolidine (0.017 mL, 0.2 mmol), potassium carbonate (46 mg, 0.34 mmol), and a catalytic amount of potassium iodide were added. The reaction was heated to 70° C. overnight. The reaction was diluted with saturated sodium bicarbonate solution and extracted with ethyl acetate. The organic extracts were dried over MgSO$_4$ and concentrated. The residue was purified by semi-prep LC-MS to give 9.6 mg of the desired product (43% yield). LC-MS (C$_{22}$H$_{26}$N$_2$O calc'd 334) m/z 335 (M+H); $^1$H NMR (300 MHz, CDCl$_3$) δ 7.58-7.53 (m, 1H), 7.26-7.25 (m, 3H), 7.12-6.99 (m, 4H), 6.37 (s, 1H), 4.10 (t, J=6 Hz, 2H), 2.99-2.90 (m, 6H), 2.24 (s, 3H), 2.22-2.14 (m, 2H), 2.00-1.90 (m, 6H).

Example 2

2-Methyl-1-[4-(3-piperidin-1-ylpropoxy)phenyl]-1H-indole

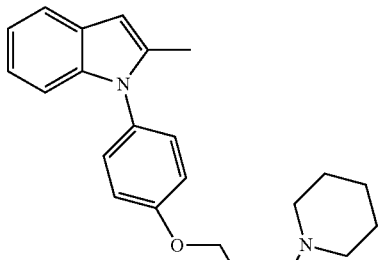

2-Methyl-1-[4-(3-piperidin-1-ylpropoxy)phenyl]-1H-indole was synthesized by a method analogous to that used for Example 1 using piperidine in place of pyrrolidine in the final step. LC-MS (C$_{23}$H$_{28}$N$_2$O calc'd 348) m/z 349 (M+H); $^1$H NMR (300 MHz, CDCl$_3$) δ 7.58-7.52 (m, 1H), 7.23-7.21 (m, 3H), 7.12-6.99 (m, 4H), 6.37 (s, 1H), 4.09 (t, J=6 Hz, 2H), 2.79-2.68 (m, 6H), 2.27 (s, 3H), 2.20-2.09 (m, 2H), 1.77-1.69 (m, 4H), 1.56-1.52 (m, 2H).

Example 3

2-Methyl-1-{4-[3-(2R-methylpyrrolidin-1-yl)propoxy]phenyl}-1H-indole

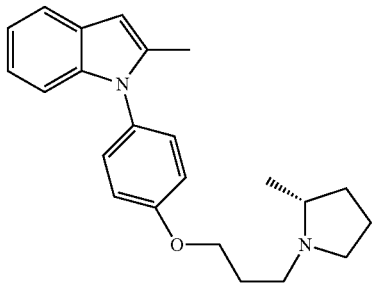

2-Methyl-1-{4-[3-(2R-methylpyrrolidin-1-yl)propoxy]phenyl}-1H-indole was synthesized by a method analogous to that used for Example 1 using (R)-2-methylpyrrolidine in place of pyrrolidine in the final step. LC-MS ($C_{23}H_{28}N_2O$ calc'd 348) m/z 349 (M+H); $^1$H NMR (300 MHz, CDCl$_3$) δ 7.58-7.52 (m, 1H), 7.26-7.25 (m, 3H), 7.12-7.00 (m, 4H), 6.37 (s, 1H), 4.16-4.05 (m, 2H), 3.46-3.39 (m, 1H), 3.22-3.13 (m, 1H), 2.75-2.63 (m, 1H), 2.57-2.42 (m, 2H), 2.27 (s, 3H), 2.21-1.55 (m, 6H), 1.25 (d, J=6.3 Hz, 3H).

Scheme 2

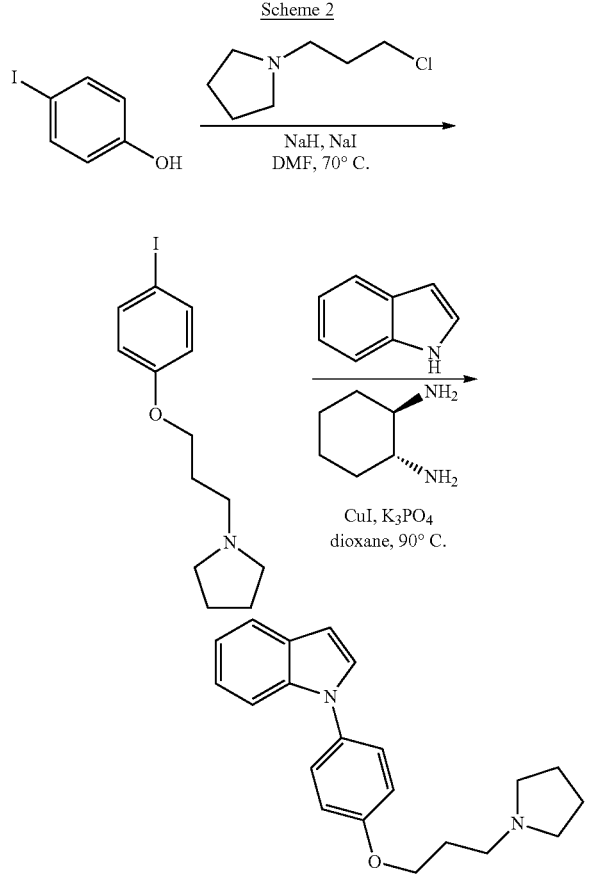

Example 4

1-[4-(3-Pyrrolidin-1-ylpropoxy)phenyl]4H-indole

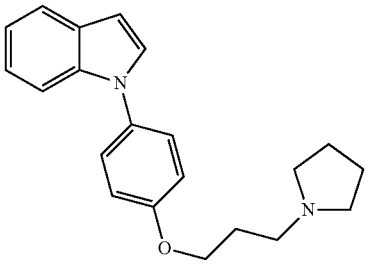

1-[3-(4-Iodophenoxy)propyl]pyrrolidine. 4-Iodophenol (2.2 g, 10 mmol) was dissolved in N,N-dimethylformamide (30 mL) under N$_2$, and sodium hydride (0.48 g, 60% dispersion in mineral oil, 12 mmol) was added in portions. 1-(3-Chloropropyl)pyrrolidine (1.77 g, 12 mmol) and sodium iodide (1.8 g, 12 mmol) were added, and the reaction mixture was stirred at 70° C. overnight. The reaction mixture was diluted with ethyl acetate and washed with water. The ethyl acetate solution was washed with 1 N HCl (2×). The acidic extracts were made basic with 2 N NaOH, then were extracted with ethyl acetate (2×). All ethyl acetate extracts were combined, dried over MgSO$_4$ and concentrated to give a yellow oil, 2.98 g (90% crude yield). LC-MS ($C_{13}H_{18}INO$ calc'd 331) m/z 332 (M+H).

1-[4-(3-Pyrrolidin-1-ylpropoxy)phenyl]1H-indole. 1-[3-(4-Iodophenoxy)propyl]-pyrrolidine (66 mg, 0.2 mmol), indole (28 mg, 0.24 mmol), copper(I) iodide (0.4 mg, 0.002 mmol), trans-1,2-diaminocyclohexane (0.0024 mmol, 0.02 mmol), and potassium phosphate tribasic (89 mg, 0.42 mmol) were stirred at 90° C. in dioxane overnight. The reaction mixture was filtered through celite and washed with dichloromethane. The filtrate was concentrated, and the resulting residue was purified by semi-prep LC-MS to give 22.4 mg of the desired product (35% yield). LC-MS ($C_{21}H_{24}N_2O$ calc'd 320) m/z 321 (M+H); $^1$H NMR (300 MHz, CDCl$_3$) δ 7.67 (d, J=6.9 Hz, 1H), 7.45 (d, J=8.4 Hz, 1H), 7.40-7.35 (m, 2H), 7.27 (d, J=3 Hz, 1H), 7.22-7.10 (m, 2H), 7.04-6.99 (m, 2H), 6.64 (d, J=3 Hz, 1H), 4.08 (t, J=6.3 Hz, 2H), 2.66 (t, J=7.2 Hz, 2H), 2.57-2.52 (m, 4H), 2.09-2.00 (m, 2H), 1.83-1.78 (m, 41-1).

Example 5

5-Methoxy-2-methyl-1-[4-(3-pyrrolidin-1-ylpropoxy)phenyl]-1H-indole

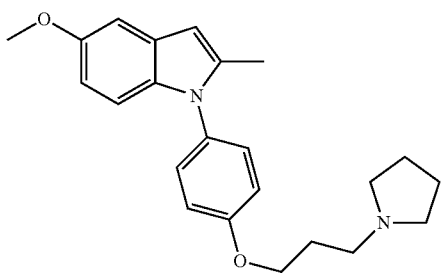

5-Methoxy-2-methyl-1-[4-(3-pyrrolidin-1-ylpropoxy)phenyl]-1H-indole was synthesized by a method analogous to that used for Example 4 using 5-methoxy-2-methylindole in place of indole in the final step. LC-MS ($C_{23}H_{28}N_2O_2$ calc'd 364) m/z 365 (M+H); $^1$H NMR (300 MHz, CDCl$_3$) δ 7.23-7.20 (m, 2H), 7.03 (d, J=2.4 Hz, 1H), 7.02-6.97 (m, 2H), 6.93 (d, J=8.7 Hz, 1H), 6.72 (dd, J=9 Hz, 2.4 Hz, 1H), 6.30 (s, 1H), 4.10 (t, J=6 Hz, 2H), 3.85 (s, 3H), 3.03-2.96 (m, 4H), 2.25 (s, 3H), 2.24-2.16 (m, 2H), 1.99-1.94 (m, 4H).

Example 6

5-Methyl-1-[4-(3-pyrrolidin-1-ylpropoxy)phenyl]-1H-indole

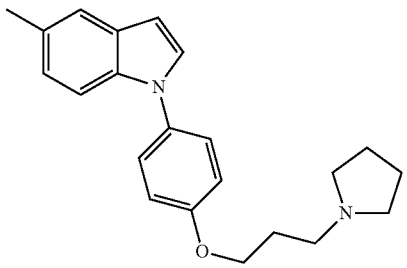

5-Methyl-1-[4-(3-pyrrolidin-1-ylpropoxy)phenyl]-1H-indole was synthesized by a method analogous to that used for Example 4 using 5-methylindole in place of indole in the final step. LC-MS ($C_{22}H_{26}N_2O$ calc'd 334) m/z 335 (M+H); $^1$H NMR (300 MHz, CDCl$_3$) δ 7.46 (s, 1H), 7.40-7.33 (m, 2H), 7.23 (d, J=3.3 Hz, 1H), 7.23 (d, J=3.3 Hz, 1H), 7.04-6.98 (m, 2H), 6.56 (d, J=3.3 Hz, 1H), 4.08 (t, J=6.3 Hz, 2H), 2.80-2.70 (m, 6H), 2.17-2.06 (m, 2H), 1.88-1.84 (m, 4H).

Example 7

5-Bromo-1-[4-(3-pyrrolidin-1-ylpropoxy)phenyl]-1H-indole

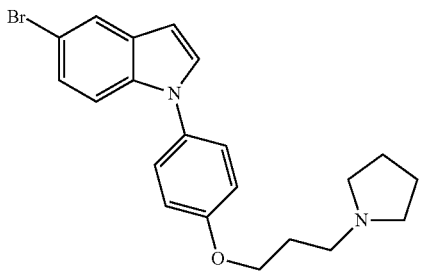

5-Bromo-1-[4-(3-pyrrolidin-1-ylpropoxy)phenyl]-1H-indole was synthesized by a method analogous to that used for Example 4 using 5-bromoindole in place of indole in the final step. LC-MS ($C_{21}H_{23}BrN_2O$ calc'd 399) m/z 400, 402 (M+H); $^1$H NMR (300 MHz, CDCl$_3$) δ 7.79 (s, 1H), 7.37 (d, J=4.8 Hz, 2H), 7.29-7.26 (m, 3H), 7.01 (d, J=8.7 Hz, 2H), 6.58 (d, J=3.3 Hz, 1H), 4.09 (t, J=6.3 Hz, 2H), 2.92-2.82 (m, 6H), 2.20-2.11 (m, 2H), 1.94-1.89 (m, 4H).

Example 8

4-Chloro-1-[4-(3-pyrrolidin-1-ylpropoxy)phenyl]-1H-indole

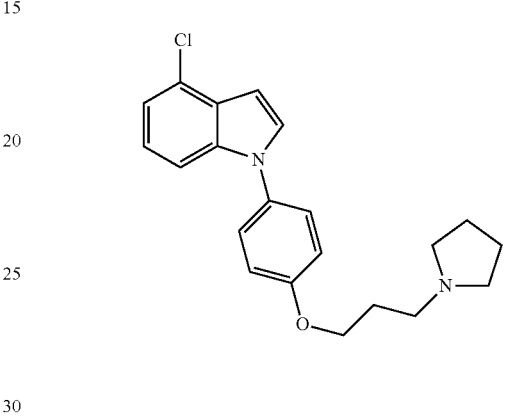

4-Chloro-1-[4-(3-pyrrolidin-1-ylpropoxy)phenyl]-1H-indole was synthesized by a method analogous to that used for Example 4 using 4-chloroindole in place of indole in the final step. LC-MS ($C_{21}H_{23}ClN_2O$ calc'd 354) m/z 355, 357 (M+H); NMR (300 MHz, CDCl$_3$) δ 7.39-7.30 (m, 4H), 7.17-7.08 (m, 2H), 7.04-6.99 (m, 2H), 6.75 (d, J=3.3 Hz, 1H), 4.09 (t, J=6 Hz, 2H), 2.97-2.89 (m, 6H), 2.22-2.13 (m, 2H), 1.96-1.92 (m, 4H).

Example 9

5-Methoxy-1-[4-(3-pyrrolidin-1-ylpropoxy)phenyl]-1H-indole

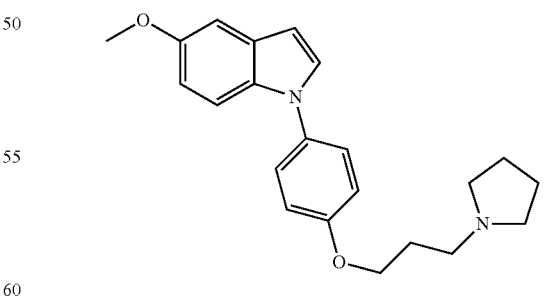

5-Methoxy-1-[4-(3-pyrrolidin-1-ylpropoxy)phenyl]-1H-indole was synthesized by a method analogous to that used for Example 4 using 5-methoxyindole in place of indole in the final step. LC-MS ($C_{22}H_{26}N_2O_2$ calc'd 350) m/z 351 (M+H).

Example 10

5-Chloro-1-[4-(3-pyrrolidin-1-ylpropoxy)phenyl]-1H-indole

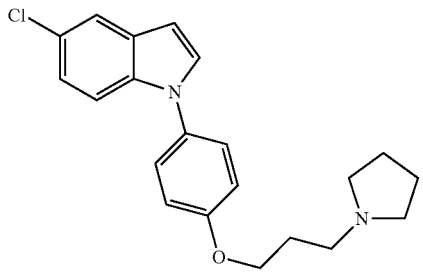

5-Chloro-1-[4-(3-pyrrolidin-1-ylpropoxy)phenyl]-1H-indole was synthesized by a method analogous to that used for Example 4 using 5-chloroindole in place of indole in the final step. LC-MS ($C_{21}H_{23}ClN_2O$ calc'd 354) m/z 355, 357 (M+H); $^1$H NMR (300 MHz, CDCl$_3$) δ 7.63 (d, J=2.1 Hz, 1H), 7.37-7.32 (m, 3H), 7.28 (d, J=3 Hz, 1H), 7.14 (dd, J=8.7 Hz, 1.8 Hz, 1H), 7.04-6.99 (m, 2H), 6.58 (d, J=3 Hz, 1H), 4.09 (t, J=6.3 Hz, 2H), 2.83-2.73 (m, 6H), 2.16-2.07 (m, 2H), 1.90-1.85 (m, 4H).

Example 11

2,5-Dimethyl-1-[4-(3-pyrrolidin-1-ylpropoxy)phenyl]-1H-indole

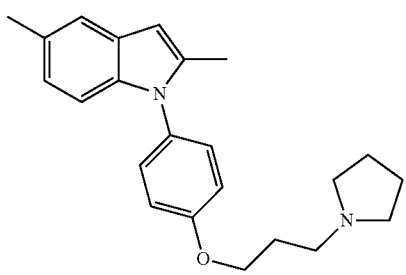

2,5-Dimethyl-1-[4-(3-pyrrolidin-1-ylpropoxy)phenyl]-1H-indole was synthesized by a method analogous to that used for Example 4 using 2,5-dimethylindole in place of indole in the final step. LC-MS ($C_{23}H_{28}N_2O$ calc'd 348) m/z 349 (M+H); $^1$H NMR (300 MHz, CDCl$_3$) δ 7.40 (s, 1H), 7.23-7.19 (m, 2H), 7.04-6.99 (m, 2H), 6.95-6.90 (m, 2H), 6.28 (s, 1H), 4.10 (t, J=6.3 Hz, 2H), 2.68 (t, J=7.2 Hz, 2H), 2.57 (m, 4H), 2.43 (s, 3H), 2.25 (s, 3H), 2.12-1.99 (m, 2H), 1.84-1.80 (m, 4H).

Example 12

6-Chloro-1-[4-(3-pyrrolidin-1-ylpropoxy)phenyl]-1H-indole

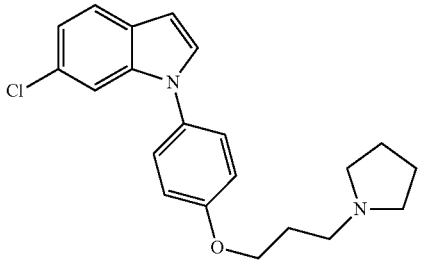

6-Chloro-1-[4-(3-pyrrolidin-1-ylpropoxy)phenyl]-1H-indole was synthesized by a method analogous to that used for Example 4 using 6-chloroindole in place of indole in the final step. LC-MS ($C_{21}H_{23}ClN_2O$ calc'd 354) m/z 355, 357 (M+H); $^1$H NMR (300 MHz, CDCl$_3$) δ 7.57 (d, J=8.4 Hz, 1H), 7.38 (s, 1H), 7.37-7.34 (m, 2H), 7.26-7.25 (m, 1H), 7.11 (dd, J=8.4 Hz, 1.8 Hz, 1H), 7.06-7.01 (m, 2H), 6.62 (d, J=3.3 Hz, 1H), 4.10 (t, J=6.3 Hz, 2H), 2.69 (t, J=7.5 Hz, 2H), 2.59 (m, 4H), 2.12-2.03 (m, 2H), 1.88-1.78 (m, 4H).

Example 13

2-Methyl-5-fluoro-1-[4-(3-pyrrolidin-1-ylpropoxy)phenyl]-1H-indole

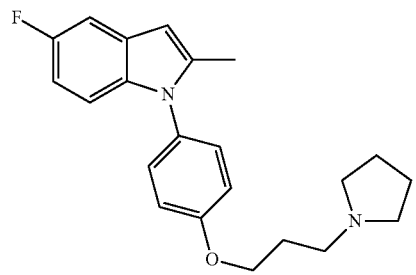

2-Methyl-5-fluoro-1-[4-(3-pyrrolidin-1-ylpropoxy)phenyl]-1H-indole was synthesized by a method analogous to that used for Example 4 using 5-fluoro-2-methylindole in place of indole in the final step. LC-MS ($C_{22}H_{25}FN_2O$ calc'd 352) m/z 353 (M+14).

Example 14

1-[3-Methoxy-4-(3-pyrrolidin-1-ylpropoxy)phenyl]-2-methyl-1H-indole

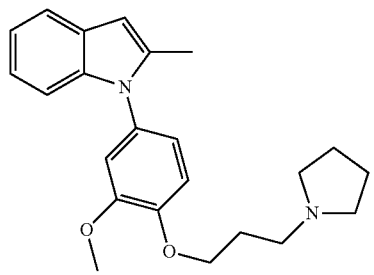

1-[3-Methoxy-4-(3-pyrrolidin-1-ylpropoxy)phenyl]-2-methyl-1H-indole was synthesized by a method analogous to that used for Example 4, using 4-bromoguaiacol in the first step rather than 4-iodophenol and 2-methylindole in the final step. LC-MS ($C_{23}H_{28}N_2O_2$ calcd 364) m/z 365 (M+H); $^1$H NMR (300 MHz, CDCl$_3$) δ 7.58-7.55 (m, 1H), 7.14-7.07 (m, 3H), 6.99 (d, J=8.7 Hz, 1H), 6.88 (dd, J=8.4 Hz, 2.4 Hz, 2H), 6.83 (d, J=2.4 Hz, 1H), 6.38 (s, 1H), 4.17 (t, J=6.3 Hz, 2H), 3.83 (s, 3H), 3.02-2.94 (m, 6H), 2.29 (s, 3H), 2.27-2.20 (m, 2H), 1.97-1.93 (m, 4H).

Example 15

1-[3-Chloro-4-(3-pyrrolidin-1-ylpropoxy)phenyl]-2-methyl-1H-indole

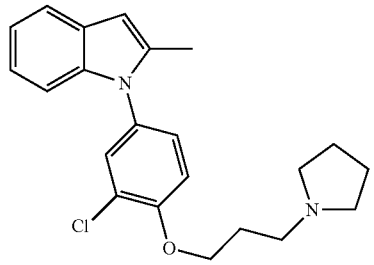

1-[3-Chloro-4-(3-pyrrolidin-1-ylpropoxy)phenyl]-2-methyl-1H-indole was synthesized by a method analogous to that used for Example 4, using 4-bromo-2-chlorophenol in the first step rather than 4-iodophenol and 2-methylindole in the final step. LC-MS ($C_{22}H_{25}ClN_2O$ calc'd 368) m/z 369, 371 (M+H); $^1$H NMR (300 MHz, CDCl$_3$) δ 7.58-7.54 (m, 1H), 7.37 (d, J=2.4 Hz, 1H), 7.20 (dd, J=8.7 Hz, 2.7 Hz, 1H), 7.11-7.02 (m, 4H), 6.38 (s, 1H), 4.19 (t, J=6.3 Hz, 2H), 2.88 (t, J=7.2 Hz, 2H), 2.77 (m, 4H), 2.24-2.15 (m, 2H), 1.91-1.87 (m, 4H).

Example 16

2-Propyl-1-[4-(3-pyrrolidin-1-ylpropoxy)phenyl]-1H-indole

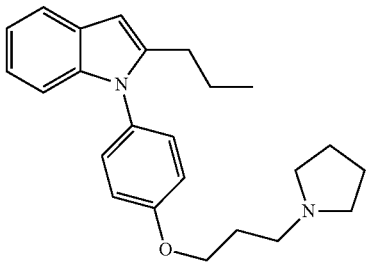

2-Propyl-1-[4-(3-pyrrolidin-1-ylpropoxy)phenyl]-1H-indole was synthesized by a method analogous to that used for Example 4 using 2-propylindole in place of indole in the final step. 2-Propylindole was prepared according to Kuyper et al. (*J. Med. Chem.* 1996, 39, 892). LC-MS ($C_{24}H_{30}N_2O$ calc'd 362) m/z 363 (M+H); $^1$H NMR (300 MHz, CDCl$_3$) δ 7.58 (m, 1H), 7.25-7.21 (m, 2H), 7.12-6.99 (m, 5H), 6.38 (s, 1H), 4.10 (t, J=6 Hz, 2H), 3.01-2.93 (m, 6H), 2.55 (t, J=7.8 Hz, 2H), 2.25-2.15 (m, 2H), 1.98-1.91 (m, 4H), 1.66-1.54 (m, 2H), 0.91 (t, J=7.5 Hz, 3H).

Scheme 3

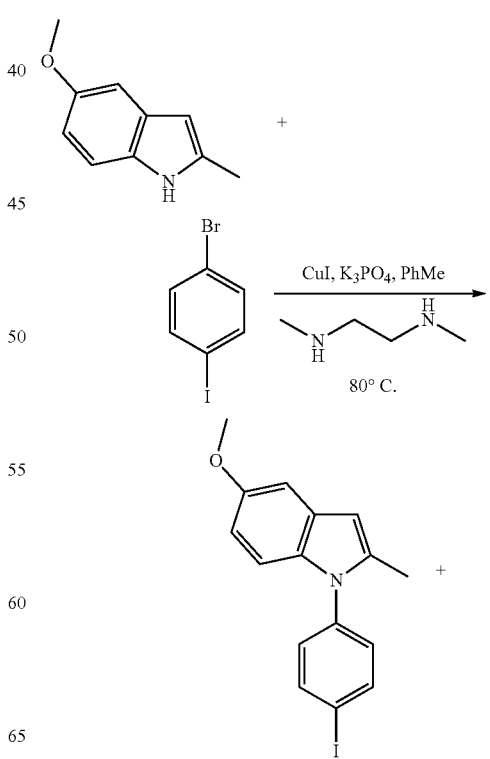

Example 17

5-Methoxy-2-methyl-1-[4-(4-pyrrolidin-1-ylbut-1-ynyl)phenyl]-1H-indole

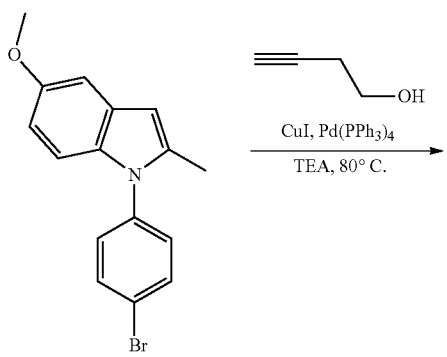

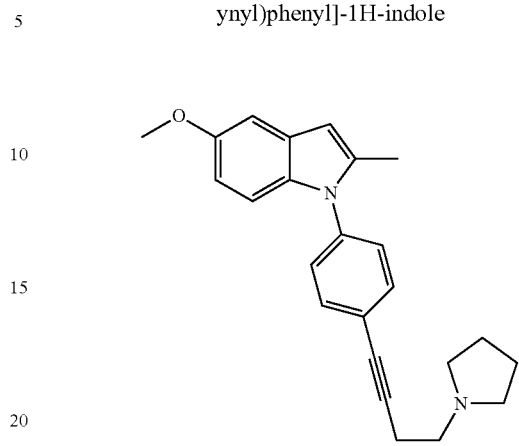

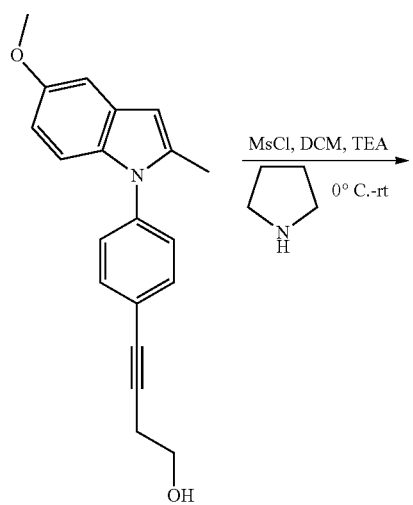

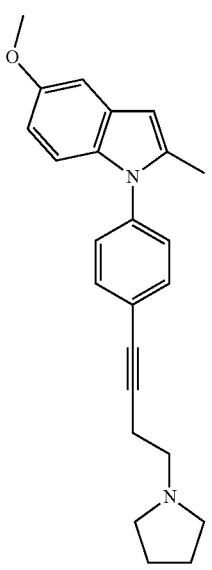

1-(4-Bromophenyl)-5-methoxy-2-methyl-1H-indole and 1-(4-Iodophenyl)-5-methoxy-2-methyl-1H-indole. 5-Methoxy-2-methylindole (500 mg, 3.1 mmol) and 1-bromo-4-iodobenzene (877 mg, 3.1 mmol) were dissolved in toluene (6 mL). To the resulting solution were added copper(I) iodide (12 mg, 0.062 mmol), potassium phosphate tribasic (1.32 g, 6.2 mmol), and N,N'-dimethylethylenediamine (6.6 µL, 0.062 mmol). The mixture was heated at 80° C. overnight, allowed to cool to room temperature and filtered through a pad of silica. The resulting solution was concentrated to give a mixture of both the bromo and the iodo halophenyl indoles, which were used without further purification (assumed quantitative).

4-[4-(5-Methoxy-2-methylindol-1-yl)phenyl]but-3-yn-1-ol. To a solution of the above mixture of indoles (50 mg) in triethylamine (1 mL) was added copper(I) iodide (6 mg, 0.03 mmol) and tetrakis(triphenylphosphine)palladium(0) (17 mg, 0.015 mmol). After 3-butyn-1-ol (15 µL, 0.20 mmol) was added, the resulting mixture was heated at 80° C. overnight. The reaction was allowed to cool and was filtered through a pad of silica. The silica was washed with ethyl acetate. Concentration gave the desired alcohol, which was used without further purification (assumed quantitative).

5-Methoxy-2-methyl-1-[4-(4-pyrrolidin-1-ylbut-1-ynyl)phenyl]-1H-indole. To a solution of 4-[4-(5-Methoxy-2-methylindol-1-yl)phenyl]but-3-yn-1-ol (60 mg, 0.19 mmol) in methylene chloride (1 mL) at 0° C. was added triethylamine (54 µL, 0.39 mmol) and methanesulfonylchloride (18 µL, 0.39 mmol). After the solution was stirred at 0° C. for 2 hours, pyrrolidine (163 µL, 1.95 mmol) was added and the reaction was allowed to warm to room temperature overnight. After the reaction was quenched with water, the organic layer was dried over MgSO$_4$, and concentrated. The residue was purified by HPLC to give the desired indole (2.8 mg). LC-MS (C$_{24}$H$_{26}$N$_2$O calc'd 358) m/z 359 (M+H); $^1$H NMR (300 MHz, CDCl$_3$) δ 7.53 (d, J=8.4 Hz, 2H), 7.26 (d, J=8.4 Hz, 2H), 7.03 (d, J=2.4 Hz, 1H), 6.99 (d, J=9.0 Hz, 1H), 6.73 (dd, J=2.7, 9.0 Hz, 1H), 6.32 (s, 1H), 3.85 (s, 3H), 2.92-2.83 (m, 4H), 2.76 (m, 4H), 2.28 (s, 3H), 1.88 (m, 4H).

Scheme 4

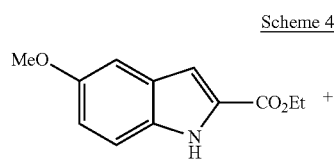

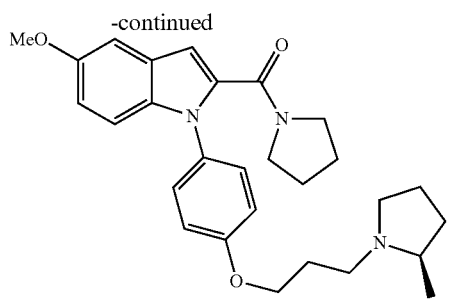

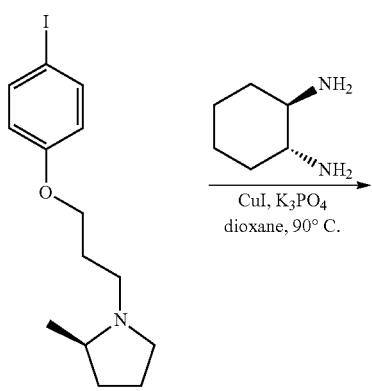

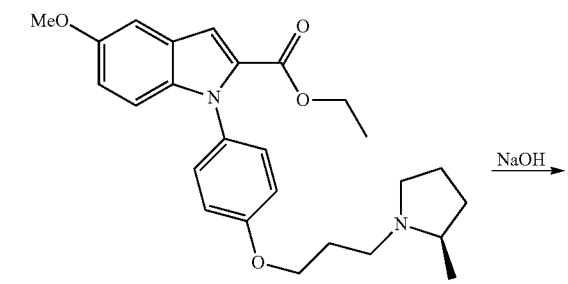

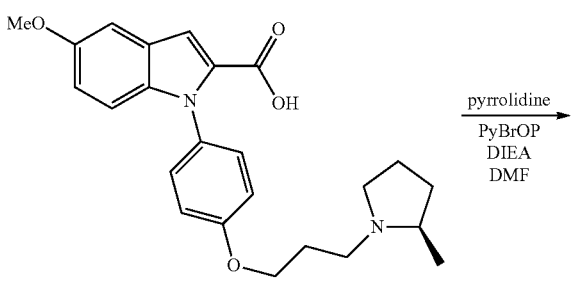

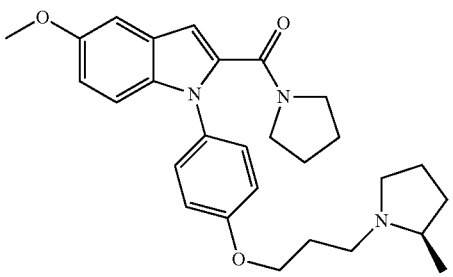

Example 18

(5-Methoxy-1-{4-[3-(2R-methylpyrrolidin-1-yl)propoxy]phenyl}-1H-indol-2-yl)pyrrolidin-1-ylmethanone

1-{4-[3-(2R-Methyl-pyrrolidin-1-yl)propoxy]phenyl}-1H-indole-2-carboxylic acid ethyl ester was synthesized by a method analogous to that used for Example 4 starting from ethyl 5-methoxyindole-2-carboxylate. 1-{4-[3-(2R-Methyl-pyrrolidin-1-yl)propoxy]phenyl}-1H-indole-2-carboxylic acid ethyl ester (0.43 mmol) was dissolved in THF (2.4 mL), methanol (1.2 mL), and water (0.4 mL), and sodium hydroxide (103 mg, 2.58 mmol) was added. The reaction mixture was heated at 50° C. overnight. A 1 N solution of HCl was added until the pH measured 7, and the solvents were evaporated. A portion of the residue (ca. 0.2 mmol) was dissolved in N,N-dimethylformamide (1 mL), and pyrrolidine (0.017 mL, 0.2 mmol), PyBrOP (0.14 g, 0.3 mmol), and diisopropylethylamine (0.104 mL, 0.6 mmol) were added. The reaction mixture was stirred overnight, and then the solvent was evaporated. The residue was purified by semi-prep LC-MS to give the desired product and a PyBrOP-related side product. The residue was further purified by $SiO_2$ chromotography with ethyl acetate, then 10% methanol/ethyl acetate, then 2% triethylamine/10% methanol/ethyl acetate to give the desired product, 15.1 mg. LC-MS ($C_{28}H_{35}N_3O_3$ calc'd 461) m/z 462 (M+H); $^1$H NMR (300 MHz, $CDCl_3$) δ 7.30 (d, J=9 Hz, 2H), 7.17 (d, J=9 Hz, 1H), 7.10 (d, J=2.4 Hz, 1H), 6.97 (d, J=8.7 Hz, 2H), 6.88 (dd, J=9 Hz, 2.4 Hz, 1H), 6.76 (s, 1H), 4.09-4.04 (m, 2H), 3.86 (s, 3H), 3.49 (t, J=6.6 Hz, 2H), 3.36 (t, J=6.2 Hz, 2H), 3.22 (dt, J=2.7 Hz, 8.7 Hz, 1H), 3.07-2.98 (m, 1H), 2.36-1.65 (m, 12 H), 1.51-1.39 (m, 1H), 1.12 (d, J=6 Hz, 3H).

Example 19

1-{4-[3-(2R-Methylpyrrolidin-1-yl)propoxy]phenyl}-1H-indole-2-carboxylic acid cyclobutylamide

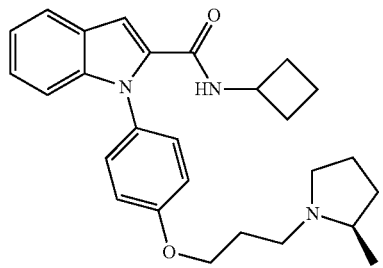

1-{4-[3-(2R-Methylpyrrolidin-1-yl)propoxy]phenyl}-1H-indole-2-carboxylic acid cyclo-butylamide was synthesized by a method analogous to that used for Example 18 using Cyclobutylamine in place of pyrrolidine. LC-MS ($C_{27}H_{33}N_3O_2$ calc'd 431) m/z 432 (M+H); $^1$H NMR (300 MHz, CDCl$_3$) δ 7.68 (d, J=7.8 Hz, 1H), 7.29-7.02 (m, 8H), 5.91 (d, J=7.8 Hz, 1H), 4.51-4.37 (m, 1H), 4.10 (t, J=6.3 Hz, 2H), 3.25-3.14 (m, 4H), 3.07-2.98 (m, 1H), 2.40-1.60 (m, 11H), 1.51-1.38 (m, 1H), 1.12 (d, J=6 Hz, 3H).

Example 20

1-{4-[3-(2R-Methylpyrrolidin-1-yl)propoxy]phenyl}-1H-indole-2-carboxylic acid cyclopentylamide

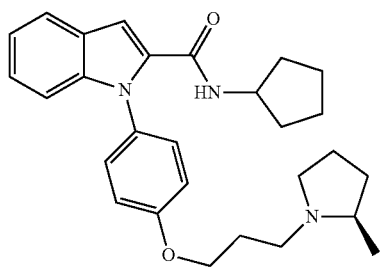

1-{4-[3-(2R-Methylpyrrolidin-1-yl)propoxy]phenyl}-1H-indole-2-carboxylic acid cyclopentylamide was synthesized by a method analogous to that used for Example 18 using cyclopentylamine in place of pyrrolidine. LC-MS ($C_{28}H_{35}N_3O_2$ calc'd 445) m/z 446 (M+H).

Example 21

1-{4-[3-(2R-Methylpyrrolidin-1-yl)propoxy]phenyl}-1H-indole-2-carboxylic acid cyclohexylamide

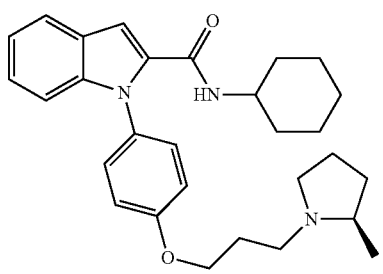

1-{4-[3-(2R-Methylpyrrolidin-1-yl)propoxy]phenyl}-1H-indole-2-carboxylic acid cyclohexylamide was synthesized by a method analogous to that used for Example 18 using cyclohexylamine in place of pyrrolidine. LC-MS ($C_{29}H_{37}N_3O_2$ calc'd 459) m/z 460 (M+H).

Example 22

1-{4-[3-(2R-Methylpyrrolidin-1-yl)propoxy]phenyl}-1H-indole-2-carboxylic acid cycloheptylamide

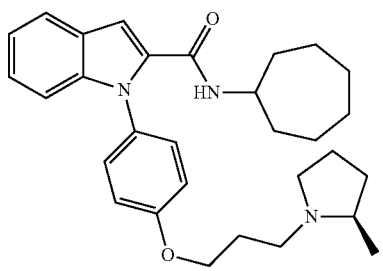

1-{4-[3-(2R-Methylpyrrolidin-1-yl)propoxy]phenyl}-1H-indole-2-carboxylic acid cycloheptylamide was synthesized by a method analogous to that used for Example 18 using cycloheptylamine in place of pyrrolidine. LC-MS ($C_{30}H_{39}N_3O_2$ calc'd 473) m/z 474 (M+H).

Example 23

(1-{4-[3-(2R-Methylpyrrolidin-1-yl)propoxy]phenyl}-1H-indol-2-yl)pyrrolidin-1-ylmethanone

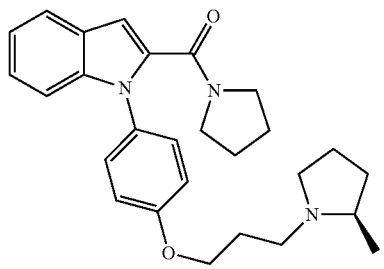

(1-{4-[3-(2R-Methylpyrrolidin-1-yl)propoxy]phenyl}-1H-indol-2-yl)pyrrolidin-1-ylmethanone was synthesized by a method analogous to that used for Example 18. LC-MS ($C_{27}H_{33}N_3O_2$ calc'd 431) m/z 432 (M+H).

Example 24

2-(3-Morpholin-4-ylpropoxy)-6,7,8,9-tetrahydropyrido[1,2-a]indole

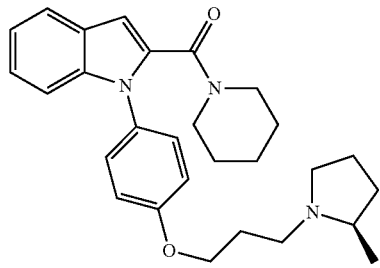

(1-{4-[3-(2R-Methylpyrrolidin-1-yl)propoxy]phenyl}-1H-indol-2-yl)piperidin-1-ylmethanone was synthesized by a method analogous to that used for Example 18 using piperidine in place of Pyrrolidine. LC-MS ($C_{28}H_{35}N_3O_2$ calc'd 445) m/z 446 (M+H).

Example 25

(1-{4-[3-(2R-Methylpyrrolidin-1-yl)propoxy]phenyl}-1H-indol-2-yl)morpholin-4-ylmethanone

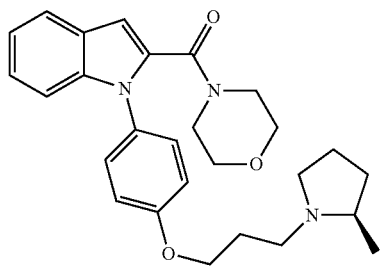

(1-{4-[3-(2R-Methylpyrrolidin-1-yl)propoxy]phenyl}-1H-indol-2-yl)morpholin-4-ylmethanone was synthesized by a method analogous to that used for Example 18 using morpholine in place of pyrrolidine. LC-MS ($C_{27}H_{33}N_3O_3$ calc'd 447) m/z 448 (M+H).

Example 26

1-{4-[3-(2R-Methylpyrrolidin-1-yl)propoxy]phenyl}-1H-indole-2-carboxylic acid butylamide

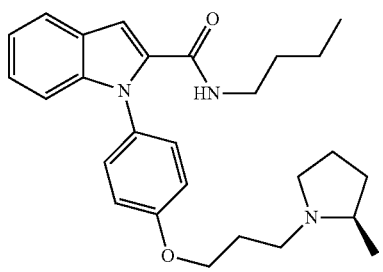

1-{4-[3-(2-Methylpyrrolidin-1-yl)propoxy]phenyl}-1H-indole-2-carboxylic acid butylamide was synthesized by a method analogous to that used for Example 18 using butylamine in place of pyrrolidine. LC-MS ($C_{27}H_{35}N_3O_2$ calc'd 433) m/z 434 (M+H).

Example 27

1-{4-[3-(2R-Methylpyrrolidin-1-yl)propoxy]phenyl}-1H-indole-2-carboxylic acid isobutylamide

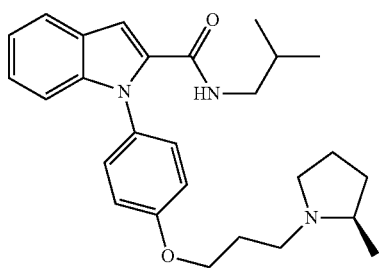

1-{4-[3-(2-Methylpyrrolidin-1-yl)propoxy]phenyl}-1H-indole-2-carboxylic acid isobutylamide was synthesized by a method analogous to that used for Example 18 using isobutylamine in place of pyrrolidine. LC-MS ($C_{27}H_{35}N_3O_2$ calc'd 433) m/z 434 (M+H).

Example 28

1-{4-[3-(2R-Methylpyrrolidin-1-yl)propoxy]phenyl}-1H-indole-2-carboxylic acid cyclohexylmethylamide

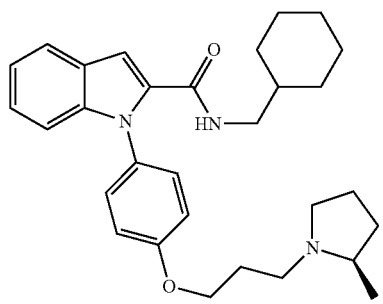

1-{4-[3-(2R-Methylpyrrolidin-1-yl)propoxy]phenyl}-1H-indole-2-carboxylic acid cyclohexylmethylamide was synthesized by a method analogous to that used for Example 18 using cyclohexylmethylamine in place of pyrrolidine. LC-MS ($C_{30}H_{39}N_3O_2$ calc'd 473) m/z 474 (M+H).

Example 29

5-Methoxy-1-{4-[3-(2R-methylpyrrolidin-1-yl)propoxy]phenyl}-1H-indole-2-carboxylic acid cyclohexylamide

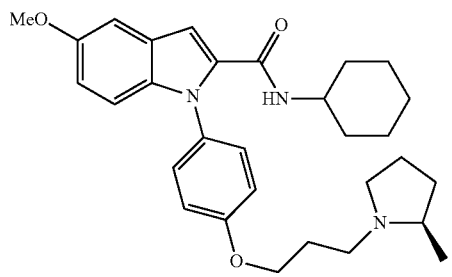

5-Methoxy-1-{4-[3-(2R-methylpyrrolidin-1-yl)propoxy]phenyl}-1H-indole-2-carboxylic acid cyclohexylamide was synthesized by a method analogous to that used for Example 18 using cyclohexylamine in place of pyrrolidine. LC-MS ($C_{30}H_{39}N_3O_3$ calc'd 489) m/z 490 (M+H).

Scheme 5

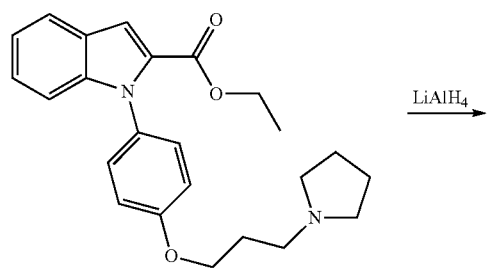

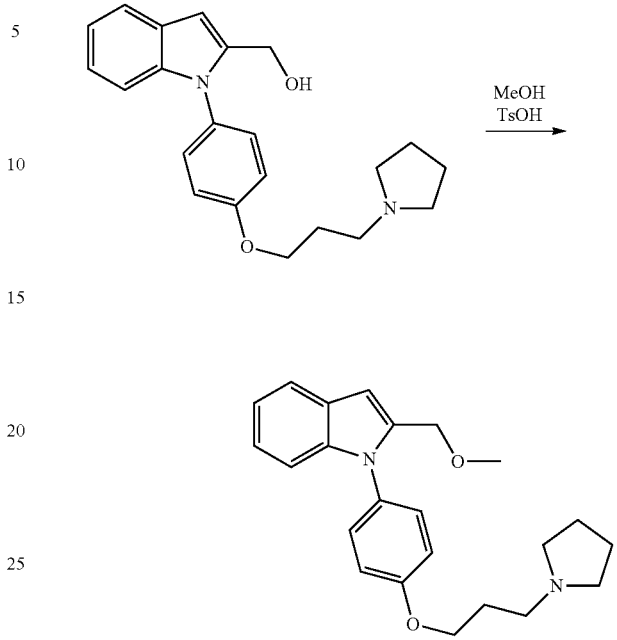

Example 30

1-[4-(3-Pyrrolidin-1-ylpropoxy)phenyl]-1H-indole-2-carboxylic acid ethyl ester

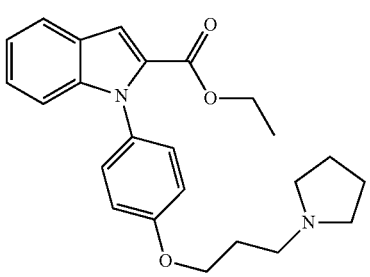

1-[4-(3-Pyrrolidin-1-ylpropoxy)phenyl]-1H-indole-2-carboxylic acid ethyl ester was synthesized by a method analogous to that used for Example 4 starting from ethyl indole-2-carboxylate. LC-MS ($C_{24}H_{28}N_2O_3$ calc'd 392) m/z 393 (M+H); $^1$H NMR (300 MHz, CDCl$_3$) δ 7.72 (d, J=7.8 Hz, 1H), 7.43 (s, 1H), 7.29-7.15 (m, 4H), 7.06 (d, J=8.4 Hz, 1H), 6.99 (d, J=8.7 Hz, 2H), 4.23 (q, J=7.2 Hz, 2H), 4.10 (t, J=6 Hz, 2H), 3.06-3.01 (m, 4H), 2.27-2.17 (m, 2H), 2.01-1.96 (m, 6H), 1.26 (t, J=7.2 Hz, 3H).

Example 31

{1-[4-(3-Pyrrolidin-1-ylpropoxy)phenyl]-1H-indol-2-yl}methanol

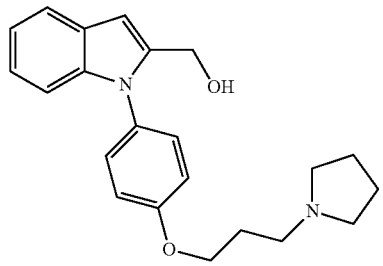

(1-[4-(3-Pyrrolidin-1-ylpropoxy)phenyl]-1H-indole-2-carboxylic acid ethyl ester (0.5 g, 1.27 mmol) was dissolved in THF (10 mL) and added dropwise to lithium aluminum hydride (1.53 mL, 1 M solution in THF, 1.53 mmol) in THF (10 mL). The reaction was stirred at 60° C. for 2 hours. Water (0.3 mL), 2 N NaOH (0.3 mL), and water (0.9 mL) were added, and the solvent was evaporated. The resulting residue was diluted with water and extracted with dichloromethane. The dichloromethane extracts were dried over $MgSO_4$ and concentrated to give a white solid, 0.36 g. A small amount of the product was purified by semi-prep LC-MS to give 3.5 mg of pure desired product. LC-MS ($C_{22}H_{26}N_2O_2$ calc'd 350) m/z 351 (M+H); $^1$H NMR (300 MHz, $CDCl_3$) δ 7.65-7.61 (m, 1H), 7.35 (d, J=8.7 Hz, 2H), 7.16-7.08 (m, 3H), 7.01 (d, J=8.7 Hz, 2H), 6.65 (s, 1H), 4.64 (s, 2H), 4.10 (t, J=6 Hz, 2H), 2.93-2.86 (m, 6H), 2.21-2.12 (m, 2H), 1.94-1.90 (m, 4H).

Example 32

2-Methoxymethyl-1-[4-(3-pyrrolidin-1-ylpropoxy)phenyl]-1H-indole

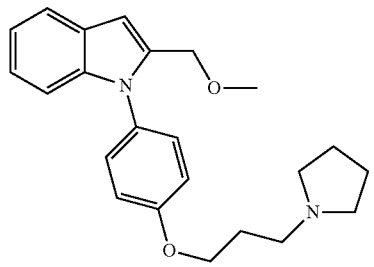

{1-[4-(3-Pyrrolidin-1-ylpropoxy)phenyl]-1H-indol-2-yl}methanol (15 mg) was dissolved in a mixture of methanol, acetonitrile, and 1 N HCl. After standing at room temperature for 2 hours, the solution was purified by semi-prep LC-MS to give 1.1 mg of the desired product. LC-MS ($C_{23}H_{28}N_2O_2$ calc'd 364) m/z 365 (M+H); $^1$H NMR (300 MHz, $CDCl_3$) δ 7.66-7.61 (m, 1H), 7.33 (d, J=9 Hz, 2H), 7.20-6.75 (m, 5H), 6.66 (s, 1H), 4.40 (s, 2H), 4.10 (t, J=6.3 Hz, 2H), 3.28 (s, 3H), 2.82-2.71 (m, 6H), 2.17-2.08 (m, 2H), 1.87 (m, 4H).

Example 33

2-Cyclohexyloxymethyl-1-[4-(3-pyrrolidin-4-ylpropoxy)phenyl]-1H-indole

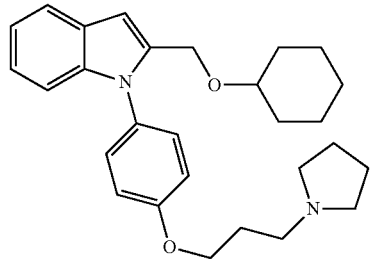

2-Cyclohexyloxymethyl-1-[4-(3-pyrrolidin-1-ylpropoxy)phenyl]-1H-indole was synthesized by a method analogous to that used for Example 32 using cyclohexanol in place of methanol. LC-MS ($C_{28}H_{36}N_2O_2$ calc'd 432) m/z 433 (M+H).

Example 34

2-Isopropoxymethyl-1-[4-(3-pyrrolidin-1-ylpropoxy)phenyl]-1H-indole

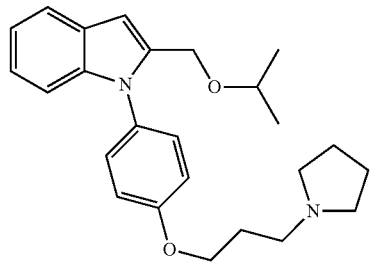

2-Isopropoxymethyl-1-[4-(3-pyrrolidin-1-ylpropoxy)phenyl]-1H-indole was synthesized by a method analogous to that used for Example 32 using isopropanol in place of methanol. LC-MS ($C_{25}H_{32}N_2O_2$ calc'd 392) m/z 393 (M+H); $^1$H NMR (300 MHz, $CDCl_3$) δ 7.63-7.61 (m, 1H), 7.35-7.32 (m, 2H), 7.14-7.07 (m, 3H), 7.01 (d, J=8.7 Hz, 2H), 6.64 (s, 1H), 4.42 (s, 2H), 4.10 (t, J=6.3 Hz, 2H), 3.58-3.48 (m, 1H), 2.76-2.38 (m, 6H), 2.08-2.02 (m, 2H), 1.83-1.71 (m, 4H), 1.08 (d, J=6 Hz, 6H).

Example 35

2-Cyclapentyloxymethyl-1-[4-(3-pyrrolidin-1-ylpropoxy)phenyl]-1H-indole

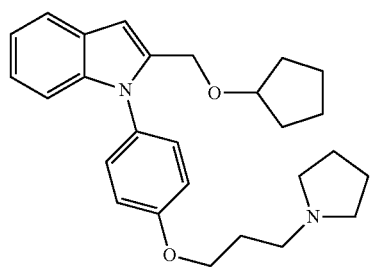

2-Cyclopentyloxymethyl-1-[4-(3-pyrrolidin-1-ylpropoxy)phenyl]-1H-indole was synthesized by a method analogous to that used for Example 32 using cyclopentanol in place of methanol. LC-MS ($C_{27}H_{34}N_2O_2$ calc'd 418) m/z 419 (M+H).

Example 36

{5-Methoxy-1-[4-(3-pyrrolidin-1-ylpropoxy)phenyl]-1H-indol-2-yl}methanol

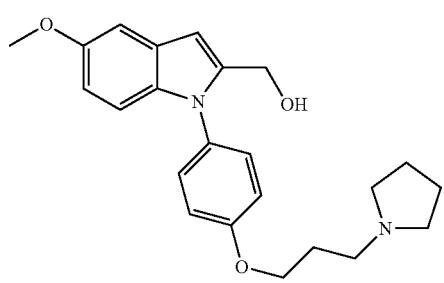

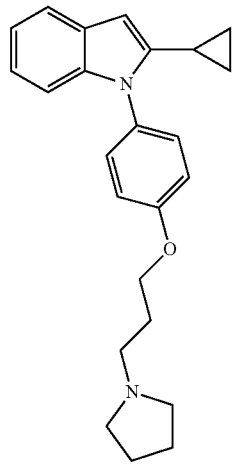

{5-Methoxy-1-[4-(3-pyrrolidin-1-ylpropoxy)phenyl]-1H-indol-2-yl}methanol was synthesized by a method analogous to that used for Example 31 starting with ethyl 5-methoxyindole-2-carboxylate. LC-MS ($C_{23}H_{28}N_2O_3$ calc'd 380) m/z 381 (M+H); $^1$H NMR (300 MHz, CDCl$_3$) δ 7.33 (d, 0.1=8.1 Hz, 2H), 7.08 (s, 1H), 6.99 (d, J=8.4 Hz, 3H), 6.80 (d, J=8.7 Hz, 1H), 6.56 (s, H), 4.61 (s, 2H), 4.07 (m, 2H), 3.85 (s, 3H), 2.83 (m, 6H), 2.14 (m, 2H), 1.91 (m, 4H).

Scheme 6

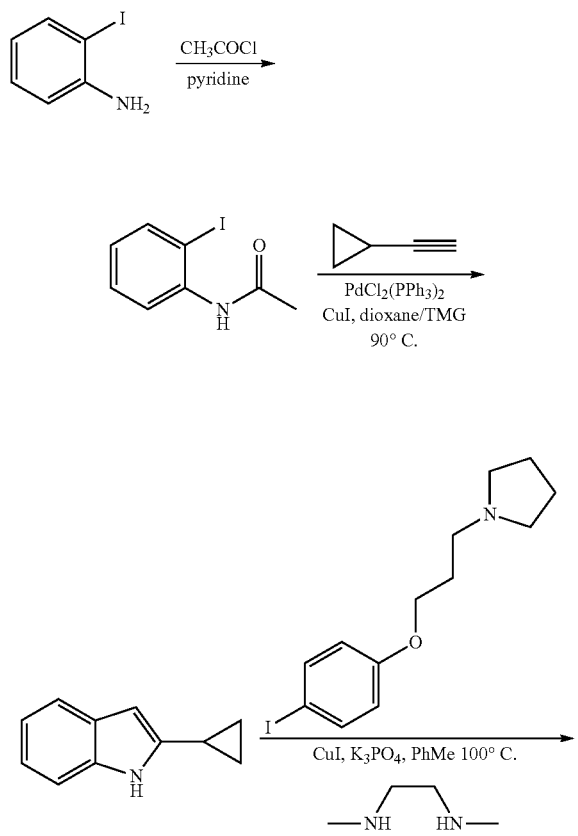

Example 37

2-Cyclopropyl-1-[4-(3-pyrrolidin-1-ylpropoxy)phenyl]-1H-indole

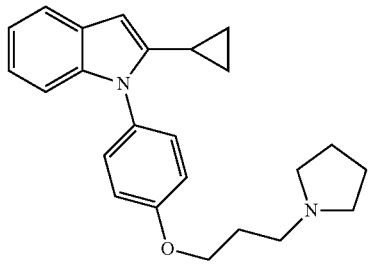

N-(2-Iodophenyl)acetamide. 2-Iodoaniline (1.00 g, 4.56 mmol) was dissolved in pyridine (5 mL) and cooled to 0° C. After acetyl chloride (314 μL, 5.94 mmol) was added, the reaction was stirred at 0° C. for 1 hour and then at room temperature for 2 hours. The reaction was diluted with 1 N HCl and extracted with ether. The organic layer was dried (MgSO$_4$) and concentrated to give the desired acetamide (assumed quantitative), which was used in the next reaction without further purification.

2-Cyclopropyl-1H-indole. To a solution of N-(2-iodophenyl)acetamide (100 mg, 0.38 mmol) in dioxane (750 mL) and 1,1,3,3-tetramethylguanidine (750 mL) was added cyclopropylacetylene (41 mL, 0.49 mmol), bis(triphenylphosphine)palladium(II) chloride (35 mg, 0.05 mmol), and copper(I) iodide (10 mg, 0.05 mmol). The reaction was stirred overnight at 80° C. The solution was cooled and partitioned between water and methylene chloride. The organic layer was dried (MgSO$_4$) and concentrated to give the uncyclized Sonagashira coupling product. Dioxane (750 mL) and 1,1,3,3-tetramethylguanidine (750 mL) were added and the reaction was stirred overnight at 90° C. The solution was again partitioned between water and methylene chloride. The organic layer was dried (MgSO$_4$) and concentrated to give the desired indole, which was used without further purification.

2-Cyclopropyl-1-[4-(3-pyrrolidin-1-ylpropoxy)phenyl]-1H-indole. To a solution of 2-cyclopropyl-1H-indole (17 mg, 0.11 mmol) and 1-[3-(4-iodophenoxy)propyl]pyrrolidine (36 mg. 0.11 mmol) in toluene (0.2 mL) was added copper iodide (0.2 mg), potassium phosphate (47 mg, 0.22 mmol), and N,N-dimethylethylenediamine (1.2 μL, 0.11 mmol). The reaction was stirred at 100° C. overnight. After cooling to room temperature, the reaction was filtered through a pad of silica. The reaction was concentrated and purified by preparative HPLC to give 1.6 mg of the desired indole. LC-MS ($C_{24}H_{28}N_2O$ calc'd 360) m/z 361 (M+H); $^1$H NMR (300 MHz, CDCl$_3$) δ 7.55-7.52 (m, 1H), 7.35-7.32 (m, 2H), 7.10-7.02 (m, 5H), 6.16 (s, 1H), 4.11 (t, J=6.3 Hz, 2H), 2.70 (t, J=7.5 Hz, 2H), 2.59 (m, 4H), 2.08 (quint, J=7.0 Hz, 1H), 1.83 (m, 2H), 1.64 (m, 4H), 0.88-0.81 (m, 2H), 0.79-0.73 (m, 2H).

Example 38

2-Propyl-1-[4-(3-pyrrolidin-1-ylpropoxy)phenyl]-1H-indole

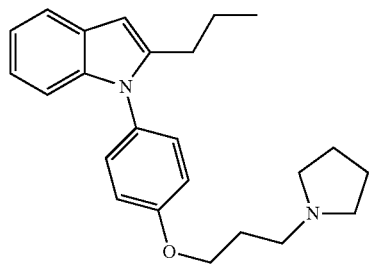

2-Propyl-1-[4-(3-pyrrolidin-1-ylpropoxy)phenyl]-1H-indole was synthesized by a method analogous to that used for Example 37 using 1-pentyne in the second step. LC-MS ($C_{24}H_{30}N_2O$ calc'd 362) m/z 363 (M+H); $^1$H NMR (300 MHz, CDCl$_3$) δ 7.61-7.54 (m, 1H), 7.25-7.21 (m, 2H), 7.09-6.99 (m, 5H), 6.38 (s, 1H), 4.10 (t, J=6 Hz, 2H), 3.01-2.93 (m, 6H), 2.55 (t, J=7.8 Hz, 2H), 2.25-2.15 (m, 2H), 1.98-1.93 (m, 4H), 1.60 (sextet, J=7.5 Hz, 2H), 0.91 (t, J=7.5 Hz, 3H).

Scheme 7

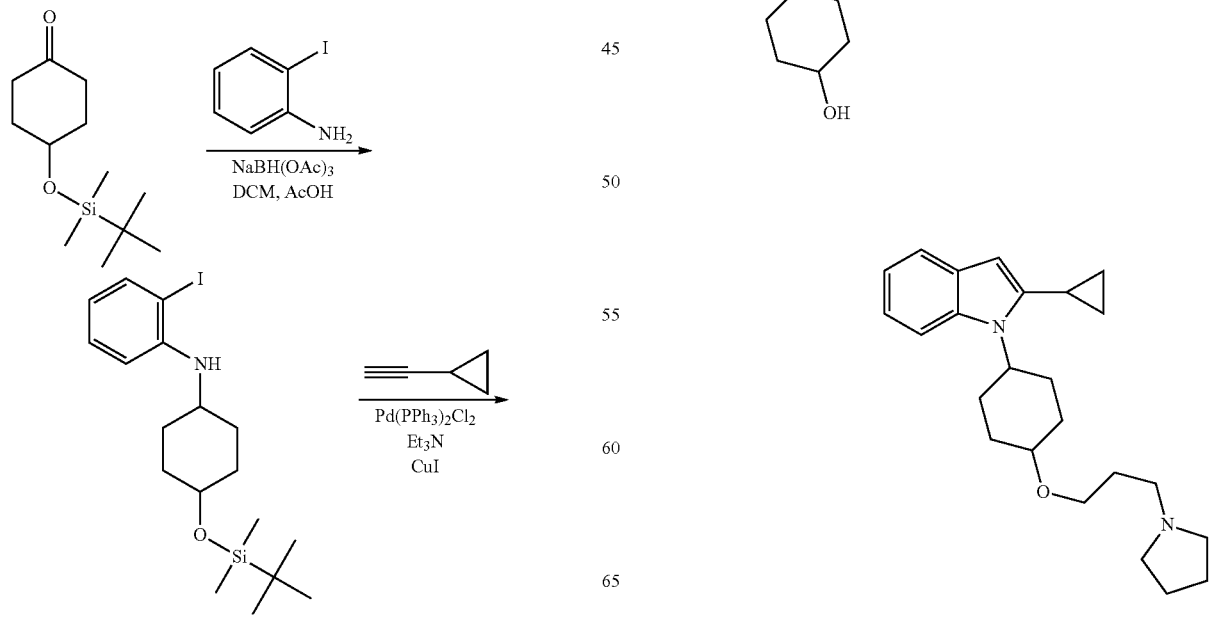

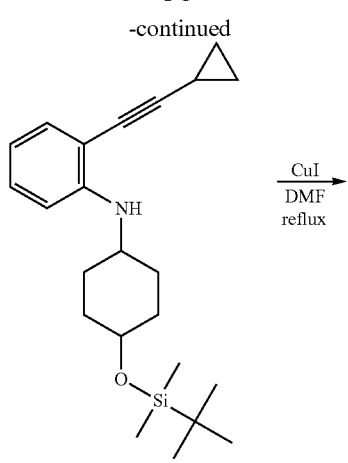

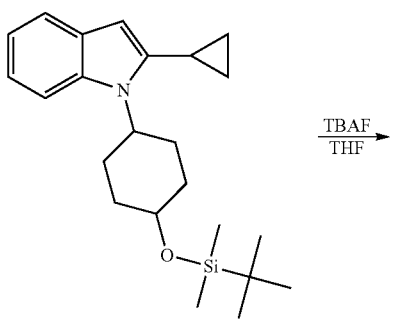

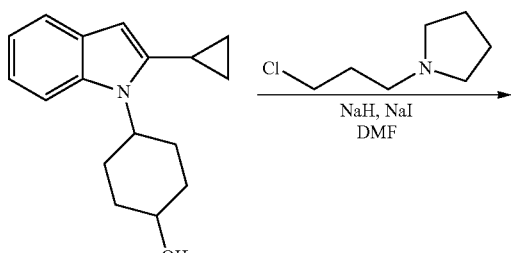

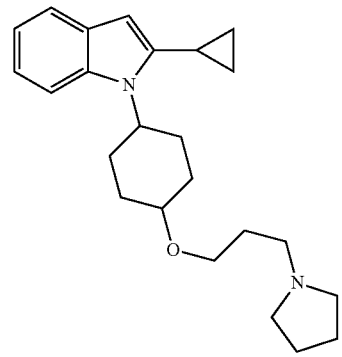

Example 39

2-Cyclopropyl-1-[4-(3-pyrrolidin-1-ylpropoxy)cyclohexyl]-1H-indole

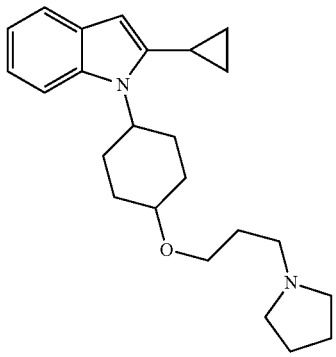

4-(tert-Butyldimethylsilanyloxy)cyclohexanone. Synthesized by literature procedure. Carreño, M. C.; Urbana, A.; Di Vitta C. *J. Org. Chem.* 1998, 63, 8320.

[4-(tert-Butyldimethylsilanyloxy)cyclohexyl]-(2-iodophenyl)amine. To a solution of 2-iodoaniline (2.5 g, 10.9 mmol) in dichloromethane (160 mL) was added 4-(tert-butyldimethylsilanyloxy)cyclohexanone (2.39 g, 10.9 mmol) and acetic acid (8 mL). After the reaction was stirred for 1 hour at room temperature, sodium triacetoxyborohydride (3.47 g, 16.4 mmol) was added and the reaction was stirred at room temperature overnight. The reaction was quenched with saturated sodium bicarbonate and extracted with dichloromethane. The organic solution was dried ($MgSO_4$) and concentrated to give 4.47 g of the desired amine, which was used without further purification. LC-MS ($C_{15}H_{30}INOSi$ calc'd 431) m/z 432 (M+H).

[4-(tert-Butyldimethylsilanyloxy)cyclohexyl]-(2-cyclopropylethynylphenyl)amine. To a solution of [4-(tert-butyldimethylsilanyloxy)cyclohexyl]-(2-iodophenyl)amine (4.47 g, 10.4 mmol) in triethylamine (70 mL) was added copper(I) iodide (198 mg, 1.04 mmol), followed by bis(triphenylphosphine)palladium(II) chloride (730 mg, 1.04 mmol) and cyclopropylacetylene (1.73 mL, 20.8 mmol). The reaction was stirred under nitrogen at room temperature overnight. After the reaction mixture was concentrated, the residue was dissolved in ether and filtered through Celite. Concentration gave the crude product, which was used without further purification in quantitative yield. LC-MS ($C_{23}H_{35}NOSi$ calc'd 369) m/z 370 (M+H).

1-[4-(tert-Butyldimethylsilanyloxy)cyclohexyl]-2-cyclopropyl-1H-indole. To a solution of [4-(tert-butyldimethylsilanyloxy)cyclohexyl]-(2-cyclopropylethynylphenyl)amine (3.84 g, 10.4 mmol) in N,N-dimethylformamide (60 mL) was added copper(I) iodide (100 mg, 0.525 mmol). After the reaction was refluxed for 48 hours, it was allowed to cool to room temperature, and the solvent was removed in vacuo. The residue was partitioned between water and dichloromethane. The dichloromethane was dried ($MgSO_4$) and concentrated to give a dark residue that was used in the next step with no further purification. LC-MS ($C_{23}H_{35}NOSi$ calc'd 369) m/z 370 (M+H).

4-(2-Cyclopropylindol-1-yl)cyclohexanol. Crude 1-[4-(tert-butyldimethylsilanyloxy)cyclohexyl]-2-cyclopropyl-1H-indole from above (10.4 mmol) was dissolved in tetrahydrofuran (150 mL), and tetrabutylammonium fluoride (21 mL, 1 M in THF, 21 mmol) was added. After the reaction was stirred for 72 hours it was concentrated and the residue partitioned between ethyl acetate and water. The organic layer was dried ($MgSO_4$), concentrated and purified by $SiO_2$ chromatography (10-50% ethyl acetate/hexanes) to give two (cis/trans) isomers (355 mg of the more polar isomer, 681 mg of the less polar isomer) of the desired alcohol. LC-MS ($C_{17}H_{21}NO$ calc'd 255) m/z 256 (M+H).

2-Cyclopropyl-1-[4-(3-pyrrolidin-1-ylpropoxy)cyclohexyl]-1H-indole. To a solution of 4-(2-cyclopropylindol-1-yl)cyclohexanol (25 mg, 0.098 mmol, more polar isomer) in N,N'-dimethylformamide (2 mL) was added sodium iodide (8 mg) and sodium hydride (6 mg, 60% dispersion in mineral oil, 0.15 mmol). After the reaction was allowed to stir at room temperature for 5 minutes, 1-(3-chloropropyl)pyrrolidine (22 mg, 0.15 mmol,) was added, and the reaction was stirred at 85° C. for 3 hours. The reaction was allowed to cool to room temperature and partitioned between water and dichloromethane. The organic layer was dried ($MgSO_4$), and concentrated. The residue was purified by preparative LCMS to give 8.0 mg of the desired amine. $^1$H NMR (300 MHz, $CDCl_3$) δ 7.50 (d, J=7.2 Hz, 1H), 7.42 (d, J=8.1 Hz, 1H), 7.12-6.99 (m, 2H), 6.14 (s, 1H), 4.64-4.53 (m, 3H), 3.58 (t, J=6.2 Hz, 2H), 3.42 (tt, J=3.9, 10.8 Hz, 1H), 2.91-2.82 (m, 4H), 2.42 (m, 2H), 2.24 (m, 2H), 2.00-1.79 (m, 9H), 1.45 (m, 2H), 0.95 (m, 2H), 0.74 (m, 2H); LC-MS ($C_{24}H_{34}N_2O$ calc'd 366) m/z 367 (M+H).

Spectral data for the product formed from the less polar isomer of 4-(2-cyclopropylindol-1-yl)cyclohexanol:

$^1$H NMR (300 MHz, $CDCl_3$) δ 7.56-7.48 (m, 2H), 7.10-6.96 (m, 2H), 6.12 (s, 1H), 4.58 (tt, J=4.2, 12.6 Hz, 1H), 3.65 (s, 1H), 3.55 (t, J=6.0 Hz, 2H), 2.78-2.62 (m, 7H), 2.15 (d, J=14.7 Hz, 2H), 2.00-1.83 (m, 8H), 1.69-1.25 (m, 4H), 0.984-0.873 (m, 2H), 0.764-0.713 (m, 2H); LC-MS ($C_{24}H_{34}N_2O$ calc'd 366) m/z 367 (M+H).

Scheme 8

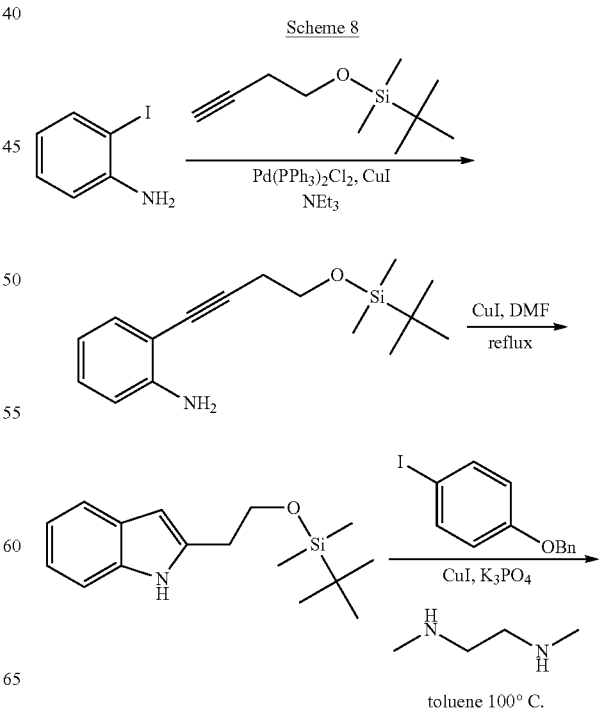

toluene 100° C.

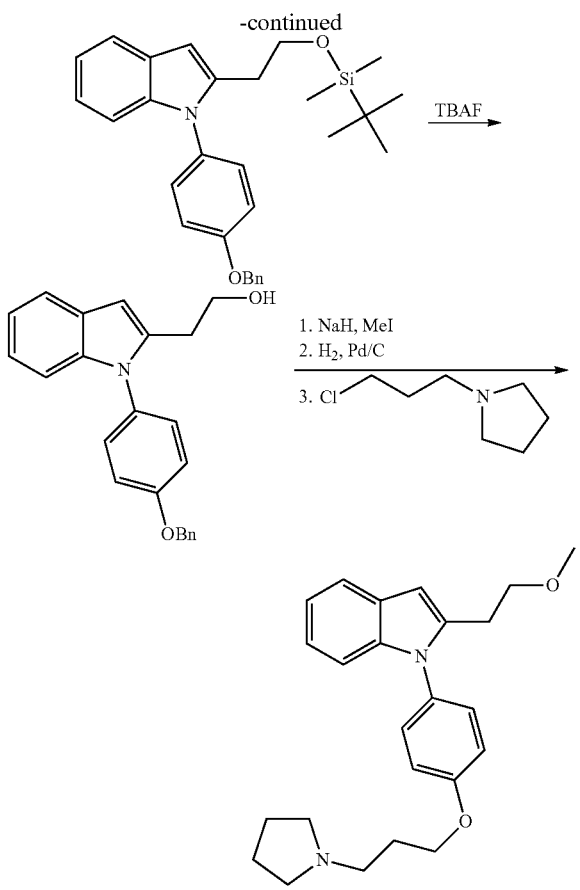

Example 40

2-(2-Methoxyethyl)-1-[4-(3-pyrrolidin-1-ylpropoxy)phenyl]-1H-indole

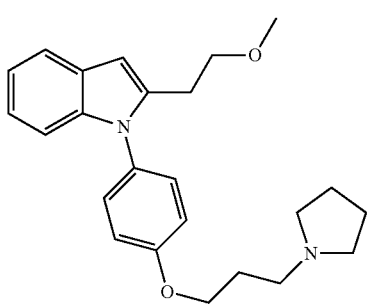

2-[4-(tert-Butyldimethylsilanyloxy)but-1-ynyl]phenylamine. 2-Iodoaniline (1.76 g, 8 mmol) was dissolved in triethylamine (50 mL) and placed under $N_2$. tert-Butylbut-3-ynyloxydimethylsilane (2.58 g, 14 mmol) was added, followed by bis(triphenylphosphine)palladium(II) chloride (30 mg, 0.042 mmol) and copper(I) iodide (7 mg, 0.036 mmol), and the reaction was stirred overnight at room temperature. Triethylamine was evaporated, and the residue was diluted with ether and filtered through Celite. The filtrate was concentrated, and the residue was purified by $SiO_2$ chromatography (5-20% ethyl acetate/hexanes) to give the desired product. The reaction was assumed to be quantitative.

2-[2-(tent-Butyldimethylsilanyloxy)ethyl]-1H-indole. 2-[4-(tert-Butyldimethylsilanyloxy)but-1-ynyl]phenylamine (8 mmol) was heated at reflux in N,N-dimethylformamide (30 mL) with copper(I) iodide (5 mg, 0.026 mmol) for 3 hours. The solvent was evaporated, and the residue was diluted with ether and filtered through Celite. The filtrate was concentrated, and the residue was purified by $SiO_2$ chromatography (5-20% ethyl acetate/hexanes) to give the desired product, 0.88 g. $^1$H NMR (300 MHz, $CDCl_3$) δ8.62 (br, 1H), 7.53 (d, J=7.5 Hz, 1H), 7.27 (d, J=7.8 Hz, 1H), 7.13-7.03 (m, 2H), 6.22 (s, 1H), 3.92 (t, J=5.7 Hz, 2H), 2.95 (t, J=5.7 Hz, 2H), 0.95 (s, 9H), 0.08 (s, 6H).

1-(4-Benzyloxyphenyl)-2-[2-(tert-butyldimethylsilanyloxy)ethyl]-1H-indole. 2-[2-(tert-Butyldimethylsilanyloxy)ethyl]-1H-indole (0.44 g, 1.6 mmol) and (4-benzyloxy)iodobenzene (0.6 g, 1.92 mmol) were dissolved in toluene (1.6 mL), and N,N-dimethylethylenediamine (0.034 mL, 0.32 mmol), copper(I) iodide (16 mg, 0.08 mmol), and potassium phosphate (0.72 g, 3.36 mmol) were added. The mixture was heated at 100° C. overnight, then filtered through a plug of silica with ether. The filtrate was concentrated, and the residue was purified by $SiO_2$ chromatography (0-10% ethyl acetate/hexanes) to give the desired product, 0.62 g. LC-MS ($C_{29}H_{35}NO_2Si$ calc'd 457) m/z 458 (M+H).

2-[1-(4-Benzyloxyphenyl)-1H-indol-2-yl]ethanol. 1-(4-Benzyloxyphenyl)-2-[2-(tert-butyldimethylsilanyloxy)ethyl]-1H-indole (0.62 mmol, 1.35 mmol) was dissolved in tetrahydrofuran (6 mL) under $N_2$, and tetrabutylammonium fluoride (1.49 mL, 1 M in tetrahydrofuran, 1.49 mmol) was added. The reaction was stirred for 2 hours, then quenched with saturated ammonium acetate. The mixture was extracted with ethyl acetate, dried over $MgSO_4$, and concentrated. The residue was passed through a plug of silica with ethyl acetate. The filtrate was concentrated to give the desired product. The reaction was assumed to be quantitative. LC-MS ($C_{23}H_{21}NO_2$ calc'd 343) m/z 344 (M+H).

1-(4-Benzyloxyphenyl)-2-(2-methoxyethyl)-1H-indole. 2-[1-(4-Benzyloxyphenyl)-1H-indol-2-yl]ethanol (0.675 mmol) was dissolved in tetrahydrofuran (5 mL) under $N_2$, and sodium hydride (81 mg, 60% dispersion in mineral oil, 2.03 mmol) was added. The reaction was heated to reflux, at which time iodomethane (0.42 mL, 6.75 mmol) was added. The reaction was stirred at reflux for 3 hours, then carefully quenched with water. The mixture was extracted with ethyl acetate, dried over $MgSO_4$, and concentrated. The residue was purified by $SiO_2$ chromatography (5-20% ethyl acetate/hexanes) to give the desired product, 0.14 g. LC-MS ($C_{24}H_{23}NO_2$ calc'd 357) m/z 358 (M+H).

4-[2-(2-Methoxyethyl)indol-1-yl]phenol. 1-(4-Benzyloxyphenyl)-2-(2-methoxyethyl)-1H-indole (0.14 g, 0.39 mmol) was dissolved in tetrahydrofuran (2 mL) and methanol (1 mL). A catalytic amount of palladium on carbon (wet, 10% dry basis) was added, and the flask was purged with $N_2$ and $H_2$. The reaction was stirred under 1 atm of $H_2$ overnight. The mixture was filtered through Celite, and the filtrate was concentrated to give the desired product. The reaction was assumed to be quantitative. LC-MS ($C_{17}H_{17}NO_2$ calc'd 267) m/z 266 (M−H).

2-(2-Methoxyethyl)-1-[4-(3-pyrrolidin-1-ylpropoxy)phenyl]-1H-indole. 4-[2-(2-Methoxyethyl)indol-1-yl]phenol (0.39 mmol) was dissolved in N,N-dimethylformamide (4 mL), and 1-(3-chloropropyl)pyrrolidine (58 mg, 0.39 mmol), sodium hydride (19 mg, 60% dispersion in mineral oil, 0.47 mmol), and sodium iodide (59 mg, 0.39 mmol) were added. The reaction was heated at 70° C. for 1.5 hours, then carefully quenched with saturated sodium bicarbonate solution. The mixture was extracted with ethyl acetate, dried over $MgSO_4$ and concentrated. The residue was purified by SiO$_2$ chromatography to give 70 mg of the desired product. LC-MS (C$_{24}$H$_{30}$N$_2$O$_2$ calc'd 378) m/z 379 (M+H); $^1$H NMR (300 MHz, CDCl$_3$) δ 7.60-7.56 (m, 1H), 7.25-7.21 (m, 2H), 7.10-7.00 (m, 5H), 6.45 (s, 1H), 4.11 (t, J=6.3 Hz, 2H), 3.57 (t, J=7.2 Hz, 2H), 3.30 (s, 3H), 2.89 (t, J=7.2 Hz, 2H), 2.74 (t, J=7.5 Hz, 2H), 2.65 (m, 4H), 2.16-2.05 (m, 2H), 1.90-1.81 (m, 4H).

2-[2-(tert-Butyldimethylsilanyloxy)ethyl]-1-[4-(3-pyrrolidin-1-ylpropoxy)phenyl]-1H-indole. 2-[2-(tert-Butyldimethylsilanyloxy)ethyl]-1H-indole (0.11 g, 0.4 mmol) and 1-[3-(4-Iodophenoxy)propyl]pyrrolidine (0.16 g, 0.48 mmol) were dissolved in toluene (0.4 mL), and N,N-dimethylethylenediamine (0.017 mL, 0.16 mmol), copper(I) iodide (30 mg, 0.16 mmol), and potassium phosphate (0.18 g, 0.84 mmol) were added. The reaction was heated at 100° C. overnight. The mixture was filtered through Celite with dichloromethane. The filtrate was concentrated, and taken forward without purification (crude product contains some starting material). LC-MS (C$_{29}$H$_{42}$N$_2$O$_2$Si calc'd 478) m/z 479 (M+H).

2-{1-[4-(3-Pyrrolidin-1-ylpropoxy)phenyl]-1H-indol-2-yl}ethanol. 2-[2-(tert-Butyldimethylsilanyloxy)ethyl]-1-[4-(3-pyrrolidin-1-ylpropoxy)phenyl]-1H-indole (0.4 mmol) was dissolved in tetrahydrofuran (2 mL) under N$_2$, and tetrabutylammonium fluoride (0.44 mL, 1 M in tetrahydrofuran, 0.44 mmol) was added. The reaction was stirred at room temperature for 3 hours, then quenched with saturated ammonium chloride. The mixture was diluted with saturated sodium bicarbonate solution and extracted with ethyl acetate. The organic extracts were dried over MgSO$_4$ and concentrated. The residue was purified by semi-prep LC-MS to give the desired product, 15.8 mg. LC-MS (C$_{23}$H$_{28}$N$_2$O$_2$ calc'd 364) m/z 365 (M+H); $^1$H NMR (300 MHz, CDCl$_3$) δ 7.61-7.59 (m, 1H), 7.24-7.20 (m, 2H), 7.13-7.07 (m, 2H), 7.03-7.00 (m, 3H), 6.48 (s, 1H), 4.09 (t, J=6.3 Hz, 2H), 3.75 (t, J=6.6 Hz, 2H), 2.89 (t, J=6.6 Hz, 2H), 2.66 (t, J=7.5 Hz, 2H), 2.60-2.49 (m, 4H), 2.10-2.01 (m, 2H), 1.85-1.76 (m, 4H).

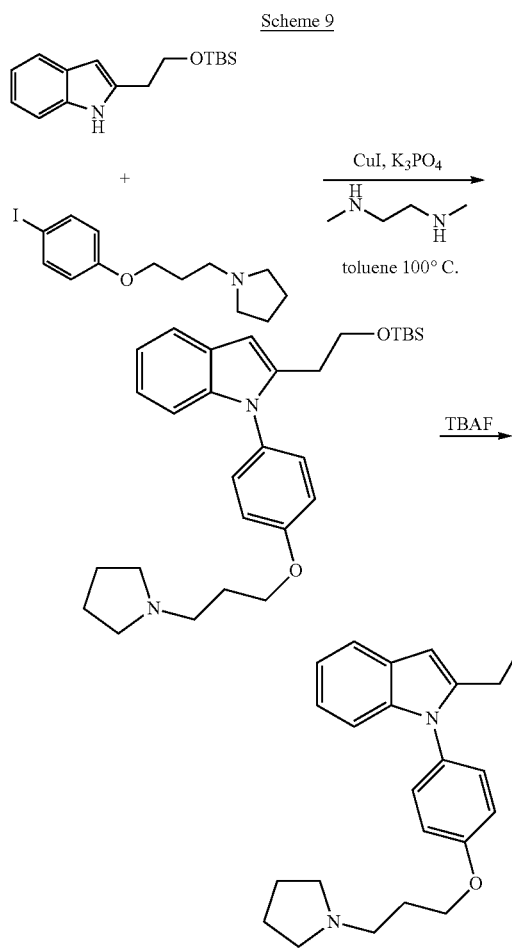

Example 41

2-{1-[4-(3-Pyrrolidin-1-ylpropoxy)phenyl]-1H-indol-2-yl}ethanol

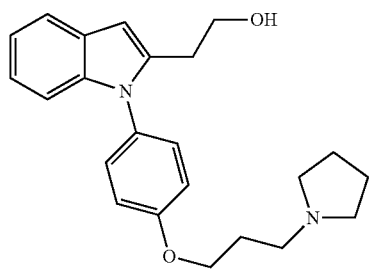

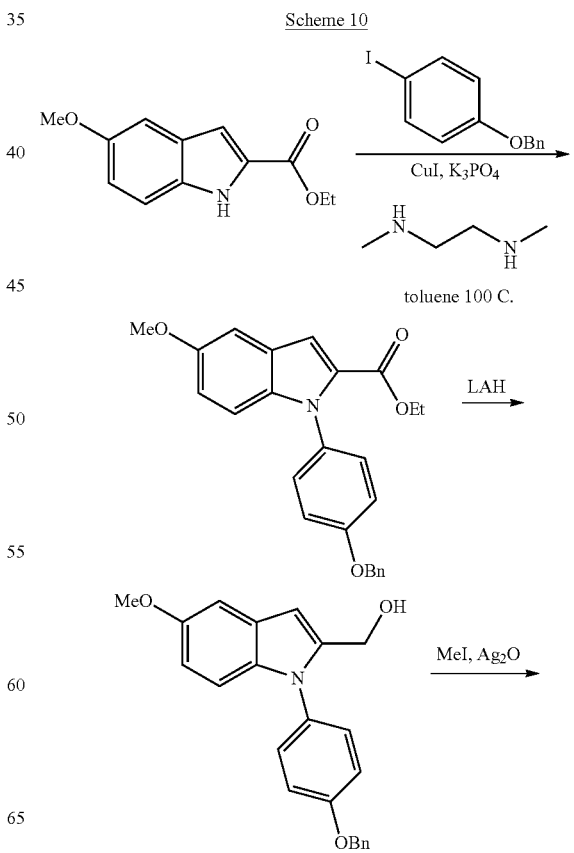

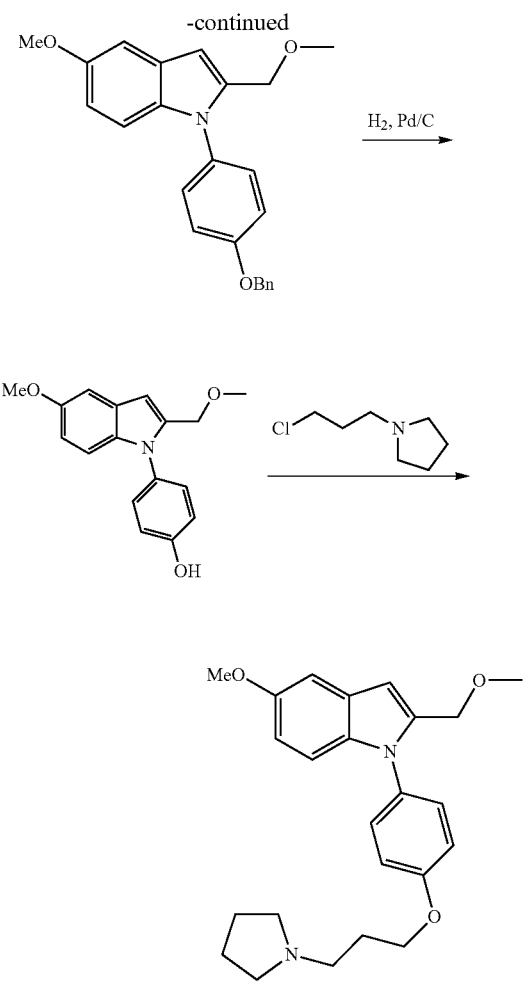

Example 42

5-Methoxy-2-methoxymethyl-1-[4-(3-pyrrolidin-1-ylpropoxy)phenyl]-1H-indole

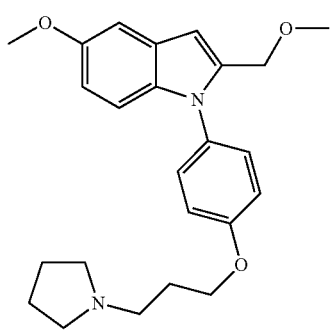

1-(4-Benzyloxyphenyl)-5-methoxy-1H-indole-2-carboxylic acid ethyl ester. 5-Methoxyindole-2-ethyl ester (0.59 g, 2.7 mmol), 1-benzyloxy-4-iodobenzene (1 g, 3.23 mmol), N,N-dimethylethylenediamine (0.057 mL, 0.54 mmol), copper(I) iodide (0.1 g, 0.54 mmol), and potassium phosphate tribasic (1.2 g, 5.67 mmol) were heated in toluene at 100° C. for 24 hours. The mixture was filtered through a plug of silica with ethyl acetate, and the filtrate was concentrated. $SiO_2$ chromatography with 5-20% ethyl acetate/hexanes gave the desired product (0.51 g, 57% yield), along with some mixed fractions (0.36 g) that were saved for future purification. LC-MS ($C_{25}H_{23}NO_4$ calc'd 401) m/z 402 (M+H).

[1-(4-Benzyloxyphenyl)-5-methoxy-1H-indol-2-yl]methanol. Lithium aluminum hydride (1.53 mL, 1 M in tetrahydrofuran, 1.53 mmol) was diluted with tetrahydrofuran (5 mL) under $N_2$, and 1-(4-benzyloxyphenyl)-5-methoxy-1H-indole-2-carboxylic acid ethyl ester (0.51 g, 1.27 mmol) in tetrahydrofuran (5 mL) was added dropwise. The reaction was stirred at reflux for 2 hours, then cooled to room temperature. Water (0.3 mL) was added carefully, followed by 2 N NaOH (0.3 mL) and water (0.9 mL). The solvent was evaporated, and the residue was partitioned between water and ethyl acetate. The organic was separated, dried over $MgSO_4$, and concentrated to give 0.41 g (88% yield) of crude product. LC-MS ($C_{23}H_{21}NO_3$ calc'd 359) m/z 360 (M+H).

1-(4-Benzyloxyphenyl)-5-methoxy-2-methoxymethyl-1H-indole. [1-(4-Benzyloxyphenyl)-5-methoxy-1H-indol-2-yl]methanol (0.2 g, 0.56 mmol) was dissolved in acetonitrile (2 mL), and iodomethane (0.35 mL, 5.6 mmol) and silver(I) oxide (0.39 g, 1.68 mmol) were added. The mixture was stirred overnight at 40° C., then cooled to room temperature and filtered through a pad of Celite. The filtrate was concentrated. $SiO_2$ chromatography with 3-50% ethyl acetate/hexanes gave 0.16 g (77% yield) of the desired product. LC-MS ($C_{24}H_{23}NO_3$ calc'd 373) m/z 374 (M+H).

4-(5-Methoxy-2-methoxymethylindol-1-yl)phenol. 1-(4-Benzyloxyphenyl)-5-methoxy-2-methoxymethyl-1H-indole (0.16 g, 0.43 mmol) was dissolved in methanol (3 mL) and tetrahydrofuran (1 mL). Palladium on carbon (0.32 g, 10% wet) and ammonium formate (0.14 g, 2.14 mmol) were added, and the reaction was stirred at reflux for 2 hours. The mixture was cooled to room temperature and filtered through a pad of Celite. The filtrate was concentrated, and the crude material taken on without purification. LC-MS ($C_{17}H_{17}NO_3$ calc'd 283) m/z 284 (M+H).

5-Methoxy-2-methoxymethyl-1-[4-(3-pyrrolidin-1-ylpropoxy)phenyl]-1H-indole. 4-(5-Methoxy-2-methoxymethylindol-1-yl)phenol (0.43 mmol) was dissolved in N,N-dimethylformamide under $N_2$. 1-(3-Chloropropyl)pyrrolidine (74 mg, 0.5 mmol), sodium hydride (20 mg, 60% wt dispersion in mineral oil, 0.5 mmol) and sodium iodide (75 mg, 0.5 mmol) were added, and the mixture was heated at 70° C. for 2 hours. The reaction was cooled to room temperature, diluted with water, and extracted with ethyl acetate. The organic extracts were dried over $MgSO_4$ and concentrated. Purification by semi-prep LC-MS gave the desired product, 67.4 mg (40% yield, 2 steps). LC-MS ($C_{24}H_{30}N_2O_3$ calc'd 394) m/z 395 (M+H); $^1$H NMR (300 MHz, $CDCl_3$) δ 7.34-7.29 (m, 2H), 7.09 (d, J=2.4 Hz, 1H), 7.04-6.98 (m, 3H), 6.82 (d, J=2.4 Hz, 1H), 6.58 (s, 1H), 4.37 (s, 2H), 4.10 (t, J=6.3 Hz, 2H), 3.86 (s, 3H), 3.28 (s, 3H), 2.69-2.64 (m, 2H), 2.58-2.54 (m, 4H), 2.11-2.01 (m, 2H), 1.83-1.79 (m, 4H).

Example 43

5-Methyl-2-methoxymethyl-1-[4-(3-pyrrolidin-1-ylpropoxy)phenyl]-1H-indole

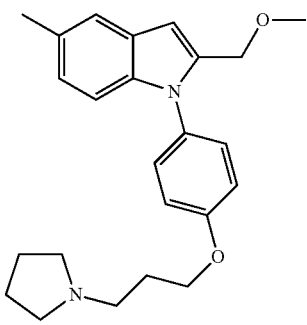

5-Methyl-2-methoxymethyl-1-[4-(3-pyrrolidin-1-ylpropoxy)phenyl]-1H-indole was synthesized by a method analogous to that used for Example 42. LC-MS ($C_{24}H_{30}N_2O_2$ calc'd 378) m/z 379 (M+H); $^1$H NMR (300 MHz, CDCl$_3$) δ 7.42-7.41 (m, 1H), 7.34-7.29 (m, 2H), 7.04-6.95 (m, 4H), 6.57 (s, 1H), 4.38 (s, 2H), 4.09 (t, J=6.3 Hz, 2H), 3.27 (s, 3H), 2.69-2.64 (m, 2H), 2.58-2.53 (m, 4H), 2.44 (s, 3H), 2.10-2.01 (m, 2H), 1.83-1.79 (m, 4H).

Example 44

5-Fluoro-2-methoxymethyl-1-[4-(3-pyrrolidin-1-ylpropoxy)phenyl]-1H-indole

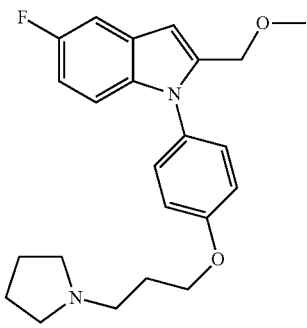

5-Fluoro-2-methoxymethyl-1-[4-(3-pyrrolidin-1-ylpropoxy)phenyl]-1H-indole was synthesized by a method analogous to that used for Example 42. LC-MS ($C_{23}H_{27}FN_2O_2$ calc'd 382) m/z 383 (M+H); $^1$H NMR (300 MHz, CDCl$_3$) δ 7.34-7.24 (m, 3H), 7.03-6.99 (m, 3H), 6.88 (td, J=9 Hz, 2.4 Hz, 1H), 6.61 (s, 1H), 4.36 (s, 2H), 4.10 (t, J=6.3 Hz, 2H), 3.28 (s, 3H), 2.69-2.64 (m, 2H), 2.57-2.53 (m, 4H), 2.10-2.01 (m, 2H), 1.83-1.79 (m, 4H).

Representative compounds of the present invention that were prepared by the procedures of Examples 1-41 were evaluated in binding assays against cells expressing human H$_3$ receptor by the following procedure.

Cell Culture

Materials

[$^{125}$I]iodoproxyfan (2000 Ci/mmol) was obtained from Amersham Bioscience Piscataway, N.J.). [$^3$H]Nα-methyhistamine (85 Ci/mmmol) was purchased from Perkin Elmers Life Science (Boston, Mass.). Calcium 3 dye kit was from Molecular Devices (Sunnyvale, Calif.). All other chemicals were either from Sigma-Aldrich (St. Louis, Mo.) or Tocris Cookson Inc. (Ellisville, Mo.).

RAGE Methodology

The human histamine H3 receptor was stably expressed in HT1080 cells containing the chimeric G-protein, Gq□i5 (Coward et al., *Anal Biochem* 1999; 270:242-8). HT1080-Gqαi5 cells were grown in alpha-modified MEM containing 10% fetal bovine serum and 7 µg/ml blasticidin at 37° C. in 5% CO$_2$/95% atmosphere. Cells (4.8×10$^9$) were irradiated with 50 rads from a $^{137}$Cs source and the pFG8-HH3 RAGE (Random Activation of Gene Expression; see Harrington et al., *Nature Biotechnology*. 2001; 19:440-45) vector was subsequently integrated into the cells via electroporation (250V, 600 µF, 50Ω). The RAGE vector pFG8-HH3 contained cDNA sequence coding for the first exon (83 amino acids) of human H3 receptor. After electroporation, cells were plated in T75 flasks and grown in alpha-modified MEM. The culture medium was replaced 48 hours after electroporation with alpha-modified MEM, 10% fetal bovine serum, 500 µg/ml hygromycin B and 3 µg/ml puromycin. Medium was replaced every four days during cell expansion. To identify RAGE activated cells expressing the H3 receptor, pools of approximately 10,000 colonies (5×10$^7$-1.5×10$^8$ cells total) were screened by PCR for the desired gene product (using primers specific to the RAGE vector and exon 2 of the H3 receptor). Pools that were found to contain the appropriate transcript, as confirmed by sequencing, were subcloned into pools of 100 cells/well. Positive 100 cells/well pools were identified by PCR, confirmed by sequencing, and subsequently subcloned to 0.8 cells/well. Once clones expressing the H3 receptor were identified by PCR analysis, assays (FLIPR or radioligand binding) were performed to confirm that the activated gene produced functional protein. The protein expression in the initial clones obtained from the RAGE library was increased by growth in the presence of methotrexate. Since the integrated RAGE vector contains the DHFR gene, such treatment selects for cells that have amplified the genetic locus containing the RAGE insert. Subclones obtained after methotrexate amplification were tested for functional activity in FLIPR assays to identify the clone that was most suitable for HTS. The final HT1080-Gqαi5 RAGE clone (RAGE-H3) expressing the human histamine H3 receptor was grown in alpha-modified MEM containing 10% fetal bovine serum, 3 µg/ml puromycin, 500 µg/ml hygromycin B, 3.2 µM methotrexate at 37° C. in 5% CO$_2$/95% atmosphere.

Membrane Preparation

RAGE-H3 cells (10$^9$) were washed twice with cold PBS, scraped off the plates, and centrifuged at 1000×g for 5 minutes. Cells were resuspended in ice-cold 10 mM Tris HCl, pH 7.4, containing 5 mM EDTA and protease inhibitor cocktail tablets (Roche Molecular Biochemicals). After incubating on ice for 10 minutes, the cells were homogenized with a dounce homogenizer or a polytron tissue grinder, and centrifuged at 1000×g for 10 minutes at 4° C. The resulting supernatant was centrifuged at 32,000×g for 30 minutes at 4° C. The membrane pellets were resuspended in 50 mM Tris HCl, pH 7.4, and stored at −80° C. until use. Protein concentration was determined by the Bradford method (Bio-Rad Laboratories, CA).

Radioligand Binding Assays

Binding assays were carried out in 96-well polypropylene plates in 50 mM Tris HCl, pH 7.4, containing 1 mM EDTA. Reaction mixtures contained 100 μl of membrane suspension, 50 of 4% DMSO, and 50 μl of increasing amounts of [$^{125}$I]iodoproxyfan (final concentration 0.0005-1.8 nM for human H3 receptor saturation binding assay). Nonspecific binding was defined by adding 10 μM clobenpropit to the reaction mixtures. Competition binding assays were performed in a reaction mixture containing 100 μl of membrane suspension (~20 μg of protein/well), 50 μl of [$^{125}$I]iodoproxyfan (final concentration of ~0.15 nM) and 50 μl of test compound. Compounds were dissolved in DMSO and then diluted with 4% DMSO; the final maximal DMSO concentration in the binding assays was 1%. Incubations were performed for 1.5 hours at room temperature and reactions were terminated by rapid filtration over glass fiber GF/C filters (Perkin Elmer, MA) using a Brandel cell harvester. The filters were pre-soaked in 0.3% polyethyleneimine for 30 minutes and were washed with 500 ml of ice-cold 50 mM Tris HCl, pH 7.4, The filters were dried, impregnated with Meltilex wax scintillate (Perkin Elmer, MA) and counted with a Betaplate scintillation counter (Perkin Elmer, MA).

Calcium Mobilization Assays

RAGE-H3 or HT1080-mH3 cells were seeded in black 384-well plates and incubated overnight at 37° C. in a 5% $CO_2$/95% atmosphere. After removing medium, cells were treated with CsCl Ringer's buffer (136 mM CsCl, 5.4 mM KCl, 5.5 mM D-Glucose, 20 mM Hepes, pH 7.4, 2.1 mM $MgCl_2$, 1.2 mM $CaCl_2$) containing the Calcium 3 dye (Molecular Device, CA) and probenecid (3.75 mM) for 60 minutes, according to manufacture's instruction. Compounds were diluted in CsCl Ringer's buffer containing 0.2% bovine serum albumin and 1.0% DMSO. The dose response of (R)-α-methylhistamine-stimulated $Ca^{2+}$ flux was measured on a Fluorometric Imaging Plate Reader (FLIPR, Molecular Devices, CA) and the concentration of (R)-α-methylhistamine to stimulate 75% of maximum response was used to test the inhibitory effect of compounds.

Data Analysis

All data were analyzed by nonlinear least squares curve fitting using Prism 4.0 software. The $K_D$ and $B_{max}$ for [$^{125}$I]iodoproxyfan were derived from the equation $RL=R_t L/(K_D+L)$, where RL is concentration of receptor-bound ligand at equilibrium, L is the free ligand concentration, and $R_t$ is the total receptor concentration (i.e., $B_{max}$). For competition binding experiments, $IC_{50}$ values (the concentration of compound producing 50% inhibition of specific binding) and Hill Coefficients (nH) were derived from fitting the data to a 4-parameter logistic equation. Apparent $K_i$ values were calculated using the Cheng-Prussof equation of $K_i=IC_{50}/(1+(L/K_D))$, where L is the ligand concentration. Agonist stimulation and antagonist inhibition in FLIPR were fitted to sigmoidal dose response curves using the equation $Y=Bottom+(Top-Bottom)/(1+10^{(LogEC_{50}-X)})$, where X is the logarithm of concentration of compounds and Y is the fluorescent response. Z' values [15] were derived to evaluate the quality of the assays. Figures are representative of two to three separate experiments performed in triplicates or quadruplicates.

The results of this assay are set forth in the following Table 1.

TABLE 1

Selected Examples

| Chemical Name | Human H3 (uM) |
|---|---|
| 2-Methyl-1-[4-(3-pyrrolidin-1-ylpropoxy)phenyl]-1H-indole<br>Example 1 | $K_i < 0.01$ |
| 2-Methyl-1-[4-(3-piperidin-1-ylpropoxy)phenyl]-1H-indole<br>Example 2 | $K_i < 0.01$ |
| 2-Methyl-1-{4-[3-(2R-methylpyrrolidin-1-yl)propoxy]phenyl}-1H-indole<br>Example 3 | $K_i < 0.01$ |
| 1-[4-(3-Pyrrolidin-1-ylpropoxy)phenyl]-1H-indole<br>Example 4 | $IC_{50} < 0.1$ |
| 5-Methoxy-2-methyl-1-[4-(3-pyrrolidin-1-ylpropoxy)phenyl]-1H-indole<br>Example 5 | $IC_{50} < 0.1$ |
| 5-Methyl-1-[4-(3-pyrrolidin-1-ylpropoxy)phenyl]-1H-indole<br>Example 6 | $IC_{50} < 1$ |
| 5-Bromo-1-[4-(3-pyrrolidin-1-ylpropoxy)phenyl]-1H-indole<br>Example 7 | $IC_{50} < 1$ |
| 4-Chloro-1-[4-(3-pyrrolidin-1-ylpropoxy)phenyl]-1H-indole<br>Example 8 | $IC_{50} < 1$ |
| 5-Methoxy-1-[4-(3-pyrrolidin-1-ylpropoxy)phenyl]-1H-indole<br>Example 9 | $IC_{50} < 1$ |
| 5-Chloro-1-[4-(3-pyrrolidin-1-ylpropoxy)phenyl]-1H-indole<br>Example 10 | $IC_{50} < 1$ |
| 2,5-Dimethyl-1-[4-(3-pyrrolidin-1-ylpropoxy)phenyl]-1H-indole<br>Example 11 | $K_i < 0.1$ |
| 6-Chloro-1-[4-(3-pyrrolidin-1-ylpropoxy)phenyl]-1H-indole<br>Example 12 | $K_i < 0.1$ |
| 2-Methyl-5-fluoro-1-[4-(3-pyrrolidin-1-ylpropoxy)phenyl]-1H-indole<br>Example 13 | $K_i < 0.01$ |
| 1-[3-Methoxy-4-(3-pyrrolidin-1-ylpropoxy)phenyl]-2-methyl-1H-indole<br>Example 14 | $IC_{50} < 1$ |
| 1-[3-Chloro-4-(3-pyrrolidin-1-ylpropoxy)phenyl]-2-methyl-1H-indole<br>Example 15 | $IC_{50} < 1$ |
| 2-Propyl-1-[4-(3-pyrrolidin-1-ylpropoxy)phenyl]-1H-indole<br>Example 16 | $K_i < 0.01$ |
| 5-Methoxy-2-methyl-1-[4-(4-pyrrolidin-1-ylbut-1-ynyl)phenyl]-1H-indole<br>Example 17 | $IC_{50} < 0.1$ |
| (5-Methoxy-1-{4-[3-(2R-methylpyrrolidin-1-yl)propoxy]phenyl}-1H-indol-2-yl)pyrrolidin-1-ylmethanone<br>Example 18 | $K_i < 0.01$ |
| 1-{4-[3-(2R-Methylpyrrolidin-1-yl)propoxy]phenyl}-1H-indole-2-carboxylic acid cyclobutylamide<br>Example 19 | $K_i < 0.01$ |
| 1-{4-[3-(2R-Methylpyrrolidin-1-yl)propoxy]phenyl}-1H-indole-2-carboxylic acid cyclopentylamide<br>Example 20 | $K_i < 0.01$ |
| 1-{4-[3-(2R-Methylpyrrolidin-1-yl)propoxy]phenyl}-1H-indole-2-carboxylic acid cyclohexylamide<br>Example 21 | $K_i < 0.1$ |
| 1-{4-[3-(2R-Methylpyrrolidin-1-yl)propoxy]phenyl}-1H-indole-2-carboxylic acid cycloheptylamide<br>Example 22 | $K_i < 0.1$ |
| (1-{4-[3-(2R-Methylpyrrolidin-1-yl)propoxy]phenyl}-1H-indol-2-yl)pyrrolidin-1-ylmethanone<br>Example 23 | $K_i < 0.01$ |
| 2-(3-Morpholin-4-ylpropoxy)-6,7,8,9-tetrahydropyrido[1,2-a]indole | $K_i < 0.01$ |

TABLE 1-continued

Selected Examples

| Chemical Name | Human H3 (uM) |
|---|---|
| Example 24<br>(1-{4-[3-(2R-Methylpyrrolidin-1-yl)propoxy]phenyl}-1H-indol-2-yl)morpholin-4-ylmethanone | $K_i < 0.01$ |
| Example 25<br>1-{4-[3-(2R-Methylpyrrolidin-1-yl)propoxy]phenyl}-1H-indole-2-carboxylic acid butylamide | $K_i < 0.01$ |
| Example 26<br>1-{4-[3-(2R-Methylpyrrolidin-1-yl)propoxy]phenyl}-1H-indole-2-carboxylic acid isobutylamide | $K_i < 0.01$ |
| Example 27<br>1-{4-[3-(2R-Methylpyrrolidin-1-yl)propoxy]phenyl}-1H-indole-2-carboxylic acid cyclohexylmethylamide | $K_i < 0.01$ |
| Example 28<br>5-Methoxy-1-{4-[3-(2R-methylpyrrolidin-1-yl)propoxy]phenyl}-1H-indole-2-carboxylic acid cyclohexylamide | $K_i < 0.01$ |
| Example 29<br>1-[4-(3-Pyrrolidin-1-ylpropoxy)phenyl]-1H-indole-2-carboxylic acid ethyl ester | $K_i < 0.01$ |
| Example 30<br>{1-[4-(3-Pyrrolidin-1-ylpropoxy)phenyl]-1H-indol-2-yl}methanol | $K_i < 0.01$ |
| Example 31<br>2-Methoxymethyl-1-[4-(3-pyrrolidin-1-ylpropoxy)phenyl]-1H-indole | $K_i < 0.01$ |
| Example 32<br>2-Cyclohexyloxymethyl-1-[4-(3-pyrrolidin-1-ylpropoxy)phenyl]-1H-indole | $K_i < 0.01$ |
| Example 33<br>2-Isopropoxymethyl-1-[4-(3-pyrrolidin-1-ylpropoxy)phenyl]-1H-indole | $K_i < 0.01$ |
| Example 34<br>2-Cyclopentyloxymethyl-1-[4-(3-pyrrolidin-1-ylpropoxy)phenyl]-1H-indole | $K_i < 0.01$ |
| Example 35<br>{5-Methoxy-1-[4-(3-pyrrolidin-1-ylpropoxy)phenyl]-1H-indol-2-yl}methanol | $K_i < 0.01$ |
| Example 36<br>2-Cyclopropyl-1-[4-(3-pyrrolidin-1-ylpropoxy)phenyl]-1H-indole | $IC_{50} < 0.1$ |
| Example 37<br>2-Propyl-1-[4-(3-pyrrolidin-1-ylpropoxy)phenyl]-1H-indole | $K_i < 0.01$ |
| Example 38<br>2-Cyclopropyl-1-[4-(3-pyrrolidin-1-ylpropoxy)cyclohexyl]-1H-indole | $K_i < 0.01$ |
| Example 39<br>2-(2-Methoxyethyl)-1-[4-(3-pyrrolidin-1-ylpropoxy)phenyl]-1H-indole | $K_i < 0.01$ |
| Example 40<br>2-{1-[4-(3-Pyrrolidin-1-ylpropoxy)phenyl]-1H-indol-2-yl}ethanol | $K_i < 0.01$ |
| Example 41<br>5-Methoxy-2-methoxymethyl-1-[4-(3-pyrrolidin-1-yl-propoxy)-phenyl]-1H-indole | $K_i < 0.01$ |
| Example 42<br>5-fluoro-2-methoxymethyl-1-[4-(3-pyrrolidin-1-yl-propoxy)-phenyl]-1H-indole | $K_i < 0.01$ |
| Example 43<br>5-methyl-2methoxymethyl-1-[4-(3-pyrrolidin-1-yl-propoxy)-phenyl]-1H-indole | $K_i < 0.01$ |
| Example 44 | |

[a] $IC_{50}$ values were determined using FLIPR.

What is claimed is:

1. A compound of the formula:

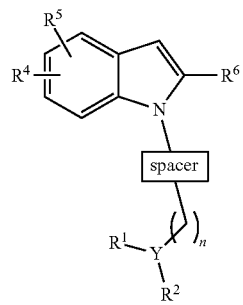

wherein spacer is

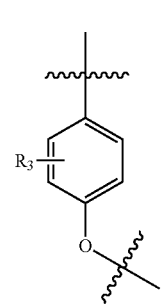

A

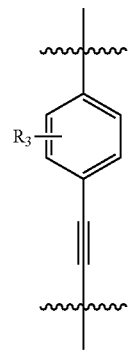

B

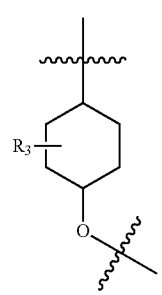

C

Y is CH or N, provided that if Y is CH then n is 0-2; if Y is N then n is 2-4;

if Y is CH then $R^1$ and $R^2$ taken together are —$(CH_2)_a$—$NR^{11}$—$(CH_2)_2$— where a is 1-2 which when taken together with Y form a piperidine or pyrrolidine ring which is optionally substituted with 1-3 groups selected from fluoro, fluoroalkyl, $(C_1$-$C_4)$alkyl, alkoxy, aryl, $(C_3$-

$C_7$)cycloalkyl, heterocycloalkyl containing 1-2 hetero atoms selected from (O, S) and ($C_1$-$C_5$)alkyl-O—($C_1$-$C_5$)alkyl; and if Y is N then $R^1$ and $R^2$ independently are ($C_1$-$C_5$)alkyl or ($C_3$-$C_6$)cycloalkyl, or $R^1$ and $R^2$ taken together with the nitrogen to which they are attached form a 5-7 member heterocyclic ring system with 0-1 additional hetero atoms selected from O and S which is optionally substituted with 1-3 ($C_1$-$C_5$)alkyl, fluoroalkyl or ($C_3$-$C_6$)cycloalkyl groups, or $R^1$ and $R^2$ taken together are —($CH_2$)$_a$—$NR^{11}$—($CH_2$)$_2$—, where a is 2-3, which when taken together with Y form a piperazine or homopiperazine ring which is optionally substituted with 1-3 groups selected from fluoro, fluoroalkyl, ($C_1$-$C_4$)alkyl, alkoxy, aryl, ($C_3$-$C_7$)cycloalkyl, heterocycloalkyl containing 1-2 hetero atoms selected from (O, S) and ($C_1$-$C_5$)alkyl-O—($C_1$-$C_5$)alkyl;

$R^3$ is 0-2 of groups selected from halogen, ($C_1$-$C_6$)alkyl, ($C_1$-$C_6$)alkoxy, ($C_3$-$C_7$)cycloalkyl, ($C_3$-$C_7$)cycloalkyl-($C_1$-$C_6$)alkyl, heterocycloalkyl containing 1-3 hetero atoms selected from (O, S) and ($C_1$-$C_3$)alkyl-O—($C_1$-$C_5$)alkyl;

$R^4$ and $R^5$ are selected independently from H, ($C_1$-$C_5$) alkyl, ($C_1$-$C_8$)alkoxy, ($C_1$-$C_5$)alkyl-O—($C_1$-$C_5$)alkyl, ($C_3$-$C_6$)cycloalkyl, aryl, $CF_3$ and halogen;

$R^6$ is $CONR^7R^8$, —($CH_2$)$_x$—O—$R^9$, alkyl, fluoroalkyl or $SO_2NR^7R^8$;

x is 1-4;

$R^7$ and $R^8$ independently are hydrogen, ($C_1$-$C_5$)alkyl or ($C_3$-$C_6$)cycloalkyl, or $R^7$ and $R^8$ together with the nitrogen to which they are attached form a 5-7 member heterocyclic ring system with 0-1 additional hetero atoms selected from O, S and N($R^{10}$), wherein the resulting ring is optionally substituted with 1-3 ($C_1$-$C_5$)alkyl or ($C_3$-$C_6$)cycloalkyl groups;

$R^9$ is hydrogen, ($C_1$-$C_5$)alkyl, ($C_3$-$C_7$)cycloalkyl or aryl;

$R^{10}$ is ($C_1$-$C_5$)alkyl, ($C_1$-$C_8$)alkoxy, ($C_1$-$C_5$)alkyl-O—($C_1$-$C_5$)alkyl, ($C_3$-$C_6$)cycloalkyl or aryl; and $R^{11}$ is ($C_1$-$C_5$)alkyl, fluoroalkyl or ($C_3$-$C_6$)cycloalkyl and the pharmaceutically acceptable salts, and individual stereoisomers thereof.

2. A compound of claim 1 selected from the group consisting of:

2-Methyl-1-[4-(3-pyrrolidin-1-ylpropoxy)phenyl]-1H-indole;
2-Methyl-1-[4-(3-piperidin-1-ylpropoxy)phenyl]-1H-indole;
2-Methyl-1-[4-(3-(2R-methylpyrrolidin-1-yl)propoxy) phenyl]-1H-indole;
1-[4-(3-Pyrrolidin-1-ylpropoxy)phenyl]-1H-indole;
5-Methoxy-2-methyl-1-[4-(3-pyrrolidin-1-ylpropoxy) phenyl]-1H-indole;
5-Methyl-1-[4-(3-pyrrolidin-1-ylpropoxy)phenyl]-1H-indole;
5-Bromo-1-[4-(3-pyrrolidin-1-ylpropoxy)phenyl]-1H-indole;
4-Chloro-1-[4-(3-pyrrolidin-1-ylpropoxy)phenyl]-1H-indole;
5-Methoxy-1-[4-(3-pyrrolidin-1-ylpropoxy)phenyl]-1H-indole;
5-Chloro-1-[4-(3-pyrrolidin-1-ylpropoxy)phenyl]-1H-indole;
2,5-Dimethyl-1-[4-(3-pyrrolidin-1-ylpropoxy)phenyl]-1H-indole;
6-Chloro-1-[4-(3-pyrrolidin-1-ylpropoxy)phenyl]-1H-indole;
2-Methyl-5-fluoro-1-[4-(3-pyrrolidin-1-ylpropoxy)phenyl]-1H-indole;
1-[3-Methoxy-4-(3-pyrrolidin-1-ylpropoxy)phenyl]-2-methyl-1H-indole;
1-[3-Chloro-4-(3-pyrrolidin-1-ylpropoxy)phenyl]-2-methyl-1H-indole;
2-Propyl-1-[4-(3-pyrrolidin-1-ylpropoxy)phenyl]-1H-indole;
5-Methoxy-2-methyl-1-[4-(4-pyrrolidin-1-ylbut-1-ynyl) phenyl]-1H-indole;
(5-Methoxy-1-{4-[3-(2R-methylpyrrolidin-1-yl)propoxy] phenyl}-1H-indol-2-yl)pyrrolidin-1-ylmethanone;
1-{4-[3-(2R-Methylpyrrolidin-1-yl)propoxy]phenyl}-1H-indole-2-carboxylic acid cyclobutylamide;
1-{4-[3-(2R-Methylpyrrolidin-1-yl)propoxy]phenyl}-1H-indole-2-carboxylic acid cyclopentylamide;
1-{4-[3-(2R-Methylpyrrolidin-1-yl)propoxy]phenyl}-1H-indole-2-carboxylic acid cyclohexylamide;
1-{4-[3-(2R-Methylpyrrolidin-1-yl)propoxy]phenyl}-1H-indole-2-carboxylic acid cycloheptylamide;
1-{4-[3-(2R-Methylpyrrolidin-1-yl)propoxy]phenyl}-1H-indol-2-yl)pyrrolidin-1-ylmethanone;
2-(3-Morpholin-4-ylpropoxy)-6,7,8,9-tetrahydropyrido [1,2-a]indole;
(1-{4-[3-(2R-Methylpyrrolidin-1-yl)propoxy]phenyl}-1H-indol-2-yl)morpholin-4-ylmethanone;
1-{4-[3-(2R-Methylpyrrolidin-1-yl)propoxy]phenyl}-1H-indole-2-carboxylic acid butylamide;
1-{4-[3-(2R-Methylpyrrolidin-1-yl)propoxy]phenyl}-1H-indole-2-carboxylic acid isobutylamide;
1-{4-[3-(2R-Methylpyrrolidin-1-yl)propoxy]phenyl}-1H-indole-2-carboxylic acid cyclohexylmethylamide;
5-Methoxy-1-{4-[3-(2R-methylpyrrolidin-1-yl)propoxy] phenyl}-1H-indole-2-carboxylic acid cyclohexylamide;
1-[4-(3-Pyrrolidin-1-ylpropoxy)phenyl]-1H-indole-2-carboxylic acid ethyl ester;
2-Cyclopropyl-1-[4-(3-pyrrolidin-1-ylpropoxy)phenyl]-1H-indole;
2-Propyl-1-[4-(3-pyrrolidin-1-ylpropoxy)phenyl]-1H-indole; and
2-Cyclopropyl-1-[4-(3-pyrrolidin-1-ylpropoxy)cyclohexyl]-1H-indole.

3. A method of treating a condition selected from obesity, age-related memory dysfunction, Parkinson's disease, attention deficit disorder, schizophrenia, epilepsy, narcolepsy, sleep apnea, insomnia, disturbed biological and circadian rhythms, hyper- and hyposomnolence, pain and migraines in a patient comprising administering an effective amount of at least one compound of claim 1 to a patient in need of such treatment.

* * * * *